United States Patent
Ashok et al.

(10) Patent No.: US 12,048,481 B2
(45) Date of Patent: Jul. 30, 2024

(54) OCULAR IMAGE DATA PROCESSING

(71) Applicant: OPTOS PLC, Dunfermline (GB)

(72) Inventors: Praveen Cheriyan Ashok, Dunfermline (GB); Michael Verhoek, Dunfermline (GB); Sriram Vikraman Sithalakshmi Amma, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 627 days.

(21) Appl. No.: 17/207,077

(22) Filed: Mar. 19, 2021

(65) Prior Publication Data
US 2021/0298592 A1    Sep. 30, 2021

(30) Foreign Application Priority Data

Mar. 30, 2020 (EP) ..................................... 20166753

(51) Int. Cl.
| | |
|---|---|
| *A61B 3/00* | (2006.01) |
| *A61B 3/10* | (2006.01) |
| *G16H 30/40* | (2018.01) |

(52) U.S. Cl.
CPC .......... *A61B 3/0025* (2013.01); *A61B 3/1005* (2013.01); *A61B 3/102* (2013.01); *G16H 30/40* (2018.01)

(58) Field of Classification Search
None
See application file for complete search history.

(56) References Cited

U.S. PATENT DOCUMENTS

| | | | | |
|---|---|---|---|---|
| 7,278,989 B2 * | 10/2007 | Vinciguerra | ........ | A61F 9/00804 606/4 |
| 2006/0227286 A1 * | 10/2006 | Hong | ....................... | G02C 7/02 351/159.01 |
| 2007/0171369 A1 * | 7/2007 | Grundig | ............... | A61B 3/0025 351/210 |

(Continued)

FOREIGN PATENT DOCUMENTS

| | | |
|---|---|---|
| EP | 1 858 402 A1 | 11/2007 |
| EP | 3 566 637 A1 | 11/2019 |

(Continued)

OTHER PUBLICATIONS

Communication and European Search Report issued on Sep. 3, 2020 in European Application No. EP 20 166 573.

(Continued)

*Primary Examiner* — Wen W Huang
(74) *Attorney, Agent, or Firm* — FAEGRE DRINKER BIDDLE & REATH

(57) ABSTRACT

A technique for generating a mapping relating values of a scan parameter of an ocular imaging apparatus that are indicative of scan locations in an eye at which the apparatus acquires digital images of imaged regions of the eye, to respective values of a conversion factor for calculating a distance between designated ocular features in the imaged regions, by: simulating light ray propagation to relate each value of the scan parameter in a sequence of scan parameter values to a corresponding location in a model eye; calculating, for each scan parameter value, a distance between the corresponding location in the model eye and a location in the model eye corresponding to an adjacent value in the sequence; and using the calculated distances to generate a respective value of the conversion factor for each scan parameter value.

14 Claims, 12 Drawing Sheets

(56) References Cited

U.S. PATENT DOCUMENTS

| | | | |
|---|---|---|---|
| 2009/0275827 A1* | 11/2009 | Aiken | A61B 5/06 600/424 |
| 2010/0114077 A1* | 5/2010 | Dai | A61F 9/00806 606/5 |
| 2010/0150415 A1 | 6/2010 | Atkinson et al. | |
| 2012/0075585 A1* | 3/2012 | Dorronsoro Diaz | A61B 3/028 351/222 |
| 2014/0327877 A1 | 11/2014 | Hemert et al. | |
| 2015/0141972 A1* | 5/2015 | Woodley | A61F 9/00827 606/5 |
| 2018/0365868 A1 | 12/2018 | Sato et al. | |
| 2019/0347774 A1 | 11/2019 | Fleming et al. | |
| 2020/0093363 A1* | 3/2020 | Saika | A61B 3/107 |
| 2020/0288976 A1* | 9/2020 | Okuda | A61B 3/10 |

FOREIGN PATENT DOCUMENTS

| | | |
|---|---|---|
| GB | 3566637 A1 | 11/2019 |
| JP | 2014-217755 A1 | 11/2014 |
| JP | 2019-195636 A1 | 11/2019 |
| WO | 2006078802 A1 | 7/2006 |
| WO | WO2006078802 A1 | 7/2006 |

OTHER PUBLICATIONS

Notice of Reasons for Rejection mailed on Jul. 26, 2022 in Japanese patent application No. 2021-058560 (6 Sheets) (English translation attached: 8 sheets).

Extended European Search Report (EESR) dated Sep. 3, 2020 issued in European patent application 20 166 753.2 (15 pages).

* cited by examiner

|  | $\varphi = \varphi_1$ | $\varphi = \varphi_2$ | $\varphi = \varphi_3$ | ... | $\varphi = \varphi_m$ |
|---|---|---|---|---|---|
| $\theta = \theta_1$ | $(x_1, y_1, z_1)$ | $(x_2, y_2, z_2)$ | $(x_3, y_3, z_3)$ |  |  |
| $\theta = \theta_2$ |  |  |  |  |  |
| $\theta = \theta_3$ |  |  |  |  |  |
| ⋮ |  |  |  |  |  |
| $\theta = \theta_m$ |  |  |  |  |  |

OCULAR IMAGE DATA PROCESSING

CROSS REFERENCE TO RELATED APPLICATION

This application claims the benefit of priority based on European Patent Application EP 20 166 753.2 filed Mar. 30, 2020, which is hereby incorporated by reference in its entirety as if set forth fully herein.

TECHNICAL FIELD

Example aspects herein generally relate to the field of data processing and, more particularly, to techniques for processing ocular imaging data.

BACKGROUND

In scanner-based ocular imaging systems, a light beam is scanned across a portion of a subject's eye (e.g. the retina) via a scanning element, and return light which has been reflected from the eye is sampled by the imaging system for each of a number of scan angles of the scanning element that are covered in the scan. A digital image of an imaged region of the portion of the eye is generated based on the sampled return light. A variety of ocular imaging systems operate according to this principle, for example scanning laser ophthalmoscopes (SLOB) that can be used for several retinal imaging modalities including fundus fluorescein angiography (FFA), indocyanine green (ICG) angiography and fundus autofluorescence (FAF), for example, and optical coherence tomography (OCT) imaging systems (among others). The acquired digital images can yield valuable information on the subject's health. For example, digital images of the retina can allow diseases of the eye, such as macular degeneration and glaucoma, as well as complications of systemic diseases such as diabetes, hypertension and other cardiovascular disease that may afflict the subject, to be detected, diagnosed and managed.

It is often invaluable in the analysis of the acquired digital images to be able to measure the size of an imaged feature of interest (e.g. a blood vessel diameter or the size of a lesion), so that any change in the size of the feature over time can be detected. By way of an example, US 2010/0150415 A1 discloses a coordinate remapping approach to calculating the size of an imaged feature, in which a measurement of a feature in a two-dimensional wide-field retinal image is defined in terms of two or more designated coordinates in the two-dimensional image, these coordinates are then mapped to equivalent coordinates in a three-dimensional model of the retina, and the size of the feature is calculated using the equivalent coordinates in a three-dimensional model.

SUMMARY

A problem with the known coordinate remapping approach to calculating ocular feature size described above is that the remapping and subsequent distance calculation operations are demanding on computing resources. These drawbacks make the known approach particularly problematic in applications where narrow-field images of the retina or other portion of the eye are acquired at a high frame rate, for example, so that many of the relatively complex remapping and subsequent distance calculations need to be performed. The inventors have recognised that, in applications of this kind (among others), it would be desirable to provide each of the digital images with information for converting a distance between points in the digital image that are expressed in terms of a number of image pixels (or other units that are used to quantify designated distances in the digital image) into physical distances between the corresponding points in the imaged portion of the eye, which may be expressed in units of length, for example metric units such as millimetres.

The present inventors have devised, in accordance with a first example aspect herein, an apparatus for processing ocular imaging data generated by a controller of an ocular imaging apparatus to evaluate a conversion factor for calculating a distance between designated ocular features in an imaged region of a portion of an eye. The apparatus comprises a scan parameter obtaining module configured to obtain from the ocular imaging data a value of a scan parameter of the ocular imaging apparatus which is indicative of a scan location, in the portion of the eye, of a scan performed by the ocular imaging apparatus to acquire a digital image of the imaged region of the portion of the eye. The apparatus further comprises a conversion factor evaluation module configured to use the obtained value of the scan parameter, and a mapping between values of the scan parameter and respective values of the conversion factor, wherein each value of the conversion factor is indicative of a simulated rate of change of distance across the portion of the eye with a function of the scan parameter for the respective value of the scan parameter, to determine a respective value of the conversion factor for converting a distance between pixels in the digital image, whose respective pixels values are acquired during imaging of the region by the ocular imaging apparatus using different respective values of the scan parameter, to a distance between corresponding locations in the region of the eye. The apparatus further comprises a data storage module configured to store the digital image in association with the determined value of the conversion factor.

The present inventors have devised, in accordance with a second example aspect herein, a computer-implemented method of processing ocular imaging data generated by a controller of an ocular imaging apparatus to evaluate a conversion factor for calculating a distance between designated ocular features in an imaged region of a portion of an eye. The method comprises obtaining from the ocular imaging data a value of a scan parameter of the ocular imaging apparatus which is indicative of a scan location in the eye of a scan performed by the ocular imaging apparatus to acquire image data defining an image of the imaged region of the portion of the eye. The method further comprises using the recorded value of the scan parameter, and a mapping between values of the scan parameter and respective values of the conversion factor, wherein each value of the conversion factor is indicative of a simulated rate of change of distance across the portion of the eye with a function of the scan parameter for the respective value of the scan parameter, to determine a respective value of the conversion factor for converting a distance between pixels in the image, whose respective pixels values are acquired during imaging of the region by the ocular imaging apparatus using different respective values of the scan parameter, to a distance between corresponding locations in the region of the eye. The method further comprises storing the image data in association with the determined value of the conversion factor.

The present inventors have devised, in accordance with a third example aspect herein, a computer-implemented method of generating a mapping which relates values of a scan parameter of an ocular imaging apparatus that are indicative of respective scan locations in a portion of an eye at which an ocular imaging apparatus is operable to acquire digital images of respective imaged regions of the portion of the eye, to respective values of a conversion factor for calculating a distance between designated ocular features in the respective imaged regions of the portion of the eye. The method comprises running a computer simulation of light ray propagation through a model of the ocular imaging apparatus and a model of the eye to generate simulation results which relate each value of the scan parameter in a sequence of the values of the scan parameter to a corresponding location in a portion of the model of the eye onto which rays of light propagating through the model of the ocular imaging apparatus impinge when the model of the ocular imaging apparatus operates in accordance with the values of the scan parameter. The method further comprises calculating, for each of the values of the scan parameter, a distance between the corresponding location in the portion of the model of the eye and a location in the portion of the model of the eye corresponding to an adjacent value in the sequence of values. The method further comprises dividing each of the calculated distances by a difference between the corresponding value of a function of the value of the scan parameter and a value of the function of the adjacent value of the scan parameter in the sequence to generate, for each of the values of the scan parameter, a respective value of the conversion factor that is indicative of a rate of change of distance across the portion of the eye with the function of the scan parameter.

The present inventors have devised, in accordance with a fourth example aspect herein, a computer program comprising computer-readable instructions which, when executed by a computer, cause the computer to execute the method according to at least one of the second example aspect and the third example aspect set out above. The computer program may be stored on a non-transitory computer-readable storage medium, or carried by a computer-readable signal.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

DETAILED DESCRIPTION OF EXAMPLE EMBODIMENTS

First Example Embodiment

Figure 1:
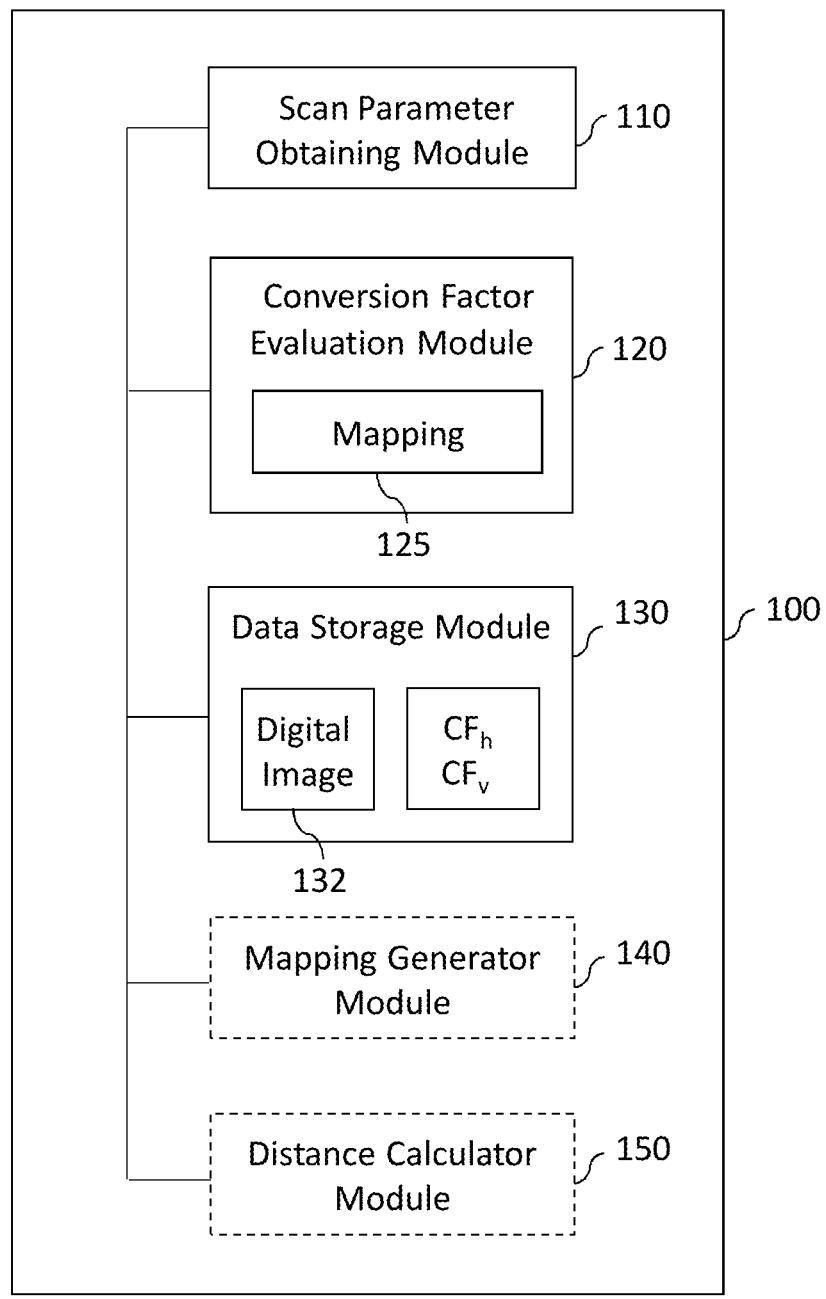
FIG. 1 is a schematic illustration of an apparatus for processing ocular imaging data according to a first example embodiment herein.

FIG. 1 is a schematic illustration of an apparatus 100 according to a first example embodiment, which is configured to process ocular imaging data generated by a controller of an ocular imaging apparatus. The apparatus 100 is configured to evaluate, based on the ocular imaging data, a conversion factor for calculating a distance between designated ocular features in a region of a portion of an eye, which region has been imaged (or is to be imaged) by the ocular imaging apparatus. The portion of the eye may, as in the present example embodiment, be the retina of the eye. However, the techniques described herein may alternatively be used to evaluate conversion factors for distance calculations relating to an imaged region of another portion of the eye, such as one or more structures in the anterior segment of the eye, for example.

As shown in FIG. 1, the apparatus 100 comprises a scan parameter obtaining module 110, a conversion factor evaluation module 120 and a data storage module 130. The apparatus 100 may, as in the present example embodiment, further comprise a mapping generator module 140 and a distance calculator module 150. Example implementations of the apparatus 100 and the functionality of its illustrated component modules are described in more detail below.

Figure 2:
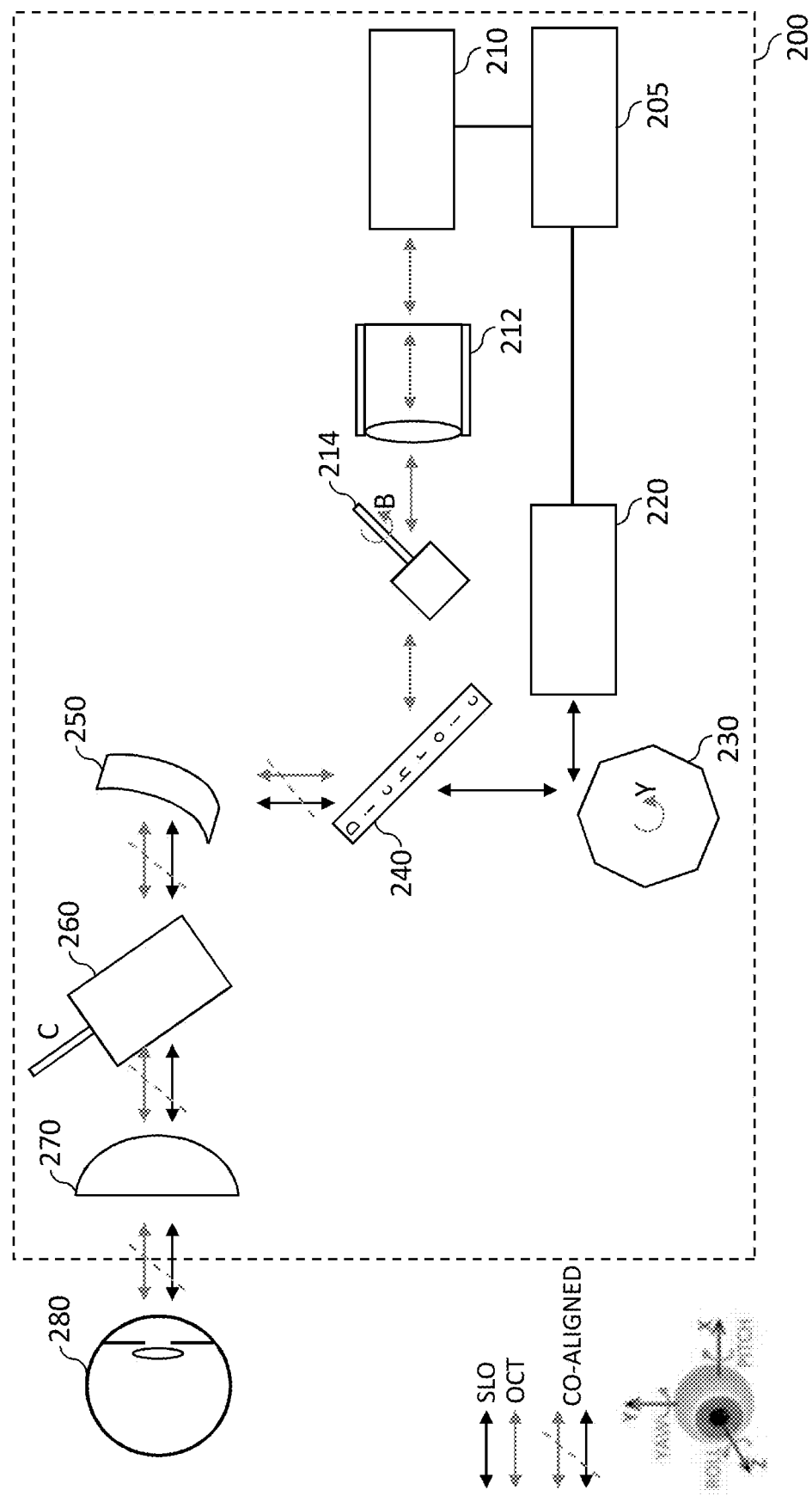
FIG. 2 is block diagram illustrating an implementation of an ocular imaging apparatus in the exemplary form of a combined SLO-OCT imaging apparatus, for acquiring imaging data which is processed by the apparatus of FIG. 1.

FIG. 2 illustrates an example implementation of an ocular imaging apparatus for generating the ocular imaging data that is to be processed by the scan parameter obtaining module 110. In the example of FIG. 2, the ocular imaging apparatus takes the form of a combined SLO-OCT ocular imaging apparatus 200, which combines scanning laser ophthalmoscope (SLO) functionality with optical coherence tomography (OCT) functionality. It should be noted, however, that the ocular imaging apparatus need not be a combined SLO-OCT ocular imaging apparatus, and could alternatively take the form of any other imaging system that employs one or more scanning elements to image the retina or other a portion of the eye, for example an SLO imaging system or an OCT imaging system.

The combined SLO-OCT imaging apparatus 200 comprises an OCT imaging part having an OCT engine 210, a focus mechanism 212, and a V-galvanometer mirror 214. Furthermore, the SLO-OCT imaging apparatus 200 comprises an SLO imaging part having an SLO engine 220 and a polygon mirror 230. The SLO-OCT imaging apparatus 200 also has a shared optical system, which includes a dichroic mirror 240, a slit mirror 250, an H-galvanometer mirror 260 and an ellipsoid mirror 270. The operation of the OCT engine 210 and the SLO engine 220 is controlled by a controller 205 of the SLO-OCT imaging apparatus 200, which may be a single piece of signal processing hardware configured to communication with both the OCT engine 210 and the SLO engine 220 (as illustrated in FIG. 2) or two separate pieces of such hardware that respectively control the OCT engine 210 and the SLO engine 220.

In FIG. 2, the SLO engine 220 comprises a SLO beam splitter, an SLO light source, an SLO photodetector, which are configured (in combination with the controller 205) to generate a digital SLO image of a retina of a subject's eye 280. The SLO light source emits SLO light which may, as in the present example, include red and green light, and near-infrared light. The beam splitter guides the SLO light from the SLO light source to the polygon mirror 230, and guides SLO light reflected from the eye 280 (namely, light reflected by the eye 280 that originates from the incident SLO light) back to the SLO photodetector.

The polygon mirror 230 reflects the SLO light from the SLO beam splitter to the shared optical system. In particular, as illustrated in the example of FIG. 2, the polygon mirror 230 scans the SLO light in a Y-direction by rotating about the illustrated axis C when driven by a drive motor (not shown). The light which has been reflected from the eye 280 and guided to the SLO imaging part via the shared optical system, is detected by the SLO photodetector, and the signal from the SLO photodetector is processed by the controller 205 to generate an SLO image, which may be an ultra-wide field (UWF) image of the retina covering up to about 80% of the retina, for example.

The OCT engine 210 is employed to generate a digital tomographic image of a part of the retina of the eye 280 and may, as in the present example, include an OCT light source, an optical coupler, a reference mirror and an OCT photodetector (not illustrated). The OCT light source emits low-coherence light, which is fed into the optical coupler and split into reference light and signal light. The reference light is guided to the reference mirror and reflected by the reference mirror to the optical coupler. The signal light is guided by the focusing mechanism 212 onto a V-galvanometer mirror, which reflects the signal light to the shared optical system. As illustrated in the example in FIG. 2, the V-galvanometer mirror 214 scans the signal light in the Y-direction (i.e. vertical direction) by rotating about an axis B when driven by a drive motor. The V-galvanometer mirror 214 also guides OCT light, which has been reflected by the eye 280 and originates from the signal light, back to the OCT engine 210. The OCT light reflected from the eye 280 is superimposed with the reference light at the optical coupler to generate interference light. The interference light is detected by the OCT photodetector, and the detection result is used by the controller 205 to generate a digital OCT image.

In FIG. 2, the dichroic mirror 240 guides the SLO light to the slit mirror 250 by causing the SLO light from the polygon mirror 230 of the SLO imaging part to be transmitted, and guides the OCT signal light to the slit mirror 250 by causing the OCT signal light from the V-galvanometer mirror 214 of the OCT imaging part to be reflected.

The slit mirror 250 reflects incident light toward the H-galvanometer mirror 260. The H-galvanometer mirror 260 reflects light from the slit mirror 250 to the ellipsoid mirror 270. Then, as illustrated in the example of FIG. 2, the H-galvanometer mirror 260 scans the emitted light in an X-direction (i.e. horizontal direction) by rotating about the axis C when driven by a drive motor (not shown).

The ellipsoid mirror 270 guides light from the H-galvanometer mirror 260 to the retina of the eye 280. Light from the ellipsoid mirror 270, which has been reflected by the eye 280, is guided to the dichroic mirror 240 in the shared optical system, along the same optical path as the emitted light. The dichroic mirror 240 guides SLO light reflected from the eye 280 to the SLO imaging part and guides OCT light reflected from the eye 280 to the OCT imaging part.

The SLO-OCT imaging apparatus 200 is operable in an SLO imaging mode, in which only the SLO imaging system operates to acquire a digital SLO image of the retina, an OCT mode, in which only the OCT imaging system operates to acquire a digital OCT image of the retina, and a combined SLO-OCT imaging mode in which both the SLO and OCT imaging systems operate to acquire a digital SLO image of the retina and a digital OCT image of the retina at the same time.

The scan location in the eye 280, at which a scan has been (or is to be) performed by the SLO-OCT imaging apparatus 200 to generate an OCT image or a SLO image, is indicated by two scan parameter values in the present example embodiment. Each of the scan parameter values provides an indication of where the scanned region of the retina (for example, a predefined reference point of the scanned region, such as a centre of the scanned region or a point at a predefined boundary of the scanned region, for example) is located along a corresponding axis of two different axes, in terms of whose coordinates any point on the retina may be specified. It should be noted, however, that a single scan parameter value may be used in other example embodiments to provide an indication of the scan location along a line (straight or curved) running across the retina, the scan parameter value providing an indication of where the scanned region of the retina (e.g. a predefined reference point of the scanned region, such as a centre of the scanned region or a point at a predefined boundary of the scanned region, for example) is located along the line. It should also be noted that a scan parameter need not be continuous variable but may alternatively be discrete, so that that the scan parameter value may be a discrete identifier which identifies the location of the scan in terms of a predetermined region of the retina from among a plurality of different predetermined regions into which the surface of the retina is divided.

It will be appreciated from the foregoing that the scan parameters can take many different forms. By way of an example, for an OCT scan performed by the SLO-OCT imaging apparatus 200, the scan parameters may respectively provide an indication of the inclination angles of scanning elements 214 and 260, which cause the OCT light beam to be scanned across the retina of the eye 280 when rotated. The inclination angle of each of the scanning elements 214 and 260 is the angle of rotation of the scanning element about its axis of rotation, relative to a reference orientation of the scanning element. An indication of each of these inclination angles may be provided in several different ways, for example as a control value in a control signal used to control the corresponding motor that sets the inclination angle of the scanning element, which value has a predetermined relationship with the inclination angle of the corresponding scanning element and thus the scan location on the retina. This relationship may be determined by simulating light ray propagation in a model of the SLO-OCT imaging apparatus 200 and a model of the eye 280, for example.

More specifically, with reference to FIG. 2, the scan location on the retina of the eye 280 of an OCT C-scan acquired by the SLO-OCT imaging apparatus 200 is determined in the present example embodiment by values of the inclination angles ($\theta$, $\varphi$) of the H-galvanometer mirror 260 and the V-galvanometer mirror 214, wherein $\theta$ denotes the inclination angle of the H-galvanometer mirror 260 and $\varphi$ denotes the inclination angle of the V-galvanometer mirror 214, when these mirrors are oriented such that the OCT light beam reflected thereby is in a geometrical centre or another reference point in the (two-dimensional) scan region, as noted above. For ease of explanation, the inclination angles $\theta$ and $\varphi$ themselves are taken to be the scan parameters for an OCT scan in the present example embodiment, although it will be understood from the foregoing that the scan parameters may be other parameters (e.g. control signal values) that are indicative of these angles.

It is noted that the OCT image captured by the SLO-OCT imaging apparatus 200 need not be a C-scan (comprising a two-dimensional array of A-scans generated in a two-dimensional OCT scan of the retina performed by the SLO-OCT imaging apparatus 200) but may alternatively be a B-scan (comprising a one-dimensional array of A-scans generated in a one-dimensional OCT scan of the retina performed by the SLO-OCT imaging apparatus 200). In either case, the scan location on the retina may be indicated by values that are indicative of angles $\theta$ and $\varphi$ at which the H-galvanometer mirror 260 and the V-galvanometer mirror 214 are set in order to direct the OCT light to the centre (or other predefined reference point) of the scan region. A scan location anywhere on the retina may thus be indicated by values of the two scan parameters $\theta$ and $\varphi$. The SLO-OCT imaging apparatus 200 may, however, be controlled by the controller 205 to perform scans (B-scans and/or C-scans) whose location can vary only along a predefined line on the retina, and a scan location along this line may be indicated by a value of a single scan parameter.

On the other hand, when performing an SLO scan using the SLO-OCT imaging apparatus 200, the location of the SLO light scanned into the eye 280 depends on the inclination angle $\theta$ of the H-galvanometer mirror 260 and the inclination angle $\alpha$ of the polygon mirror 230. Therefore, for a two-dimensional SLO image captured by the SLO-OCT imaging apparatus 200, the scan parameters may comprise a horizontal scan parameter indicative of an inclination angle of the H-galvanometer mirror 260, and a vertical scan parameter indicative of an inclination angle $\alpha$ of the polygon mirror 230.

Although the scan parameters are indicative of inclination angles of the scanning elements that are used by the SLO-OCT imaging apparatus 200 to perform the scan in order to generate an OCT or SLO image, it is noted that the scan parameters are not limited to these examples, and may be any of one or more other parameters whose values can provide an indication of the scan location on the retina or other portion of the eye 280. For example, the scan parameter may alternatively provide an indication of an angle that is subtended by the scanned light beam when propagating to the retina of the eye 280, and a reference direction of the eye (e.g. an optical axis of the lens of the eye 280) or a reference direction defined in the SLO-OCT imaging apparatus 200. This kind of alternative is described in more detail below, with reference to the second example embodiment.

Figure 3:
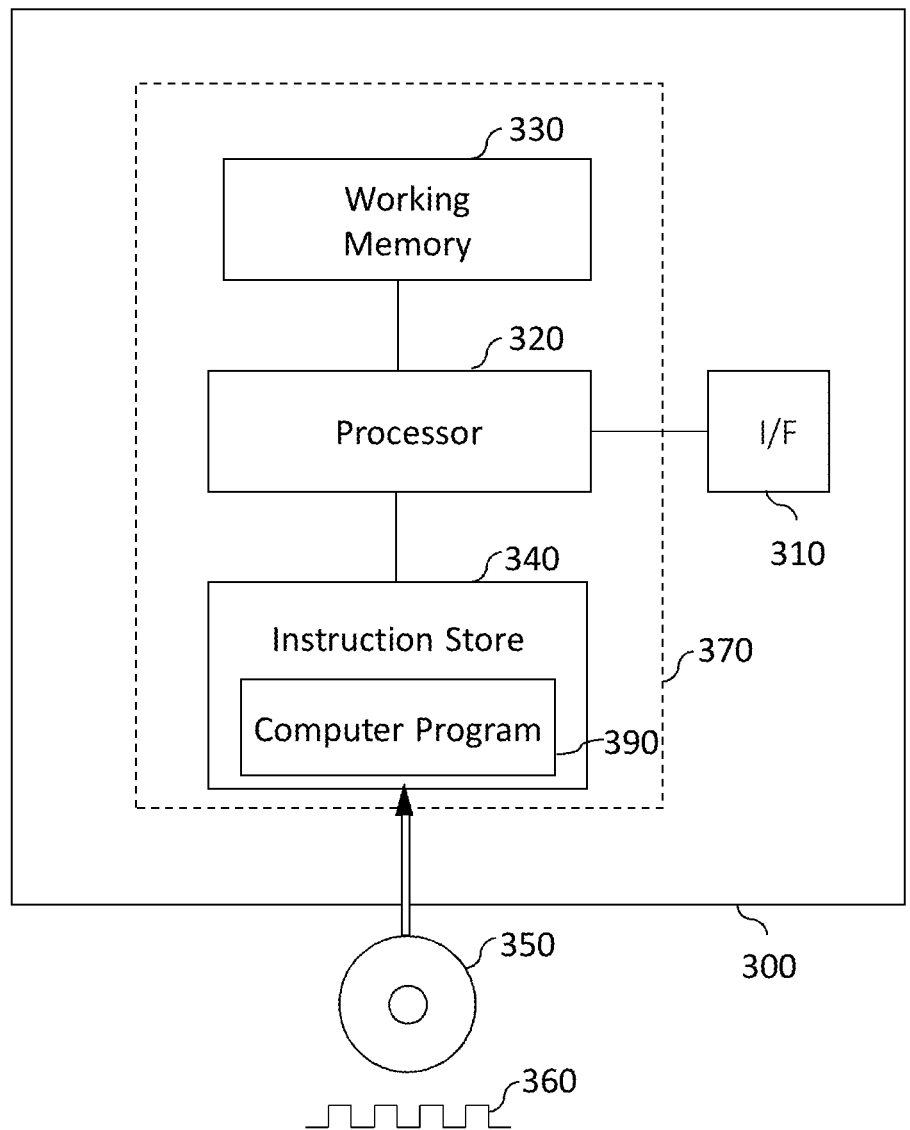
FIG. 3 is a block diagram illustrating an example implementation of the apparatus of the first example embodiment in programmable signal processing hardware.

FIG. 3 is a schematic illustration of how the apparatus 100 may be implemented in programmable signal processing hardware. The signal processing apparatus 300 shown in FIG. 3 comprises an interface module 310 for receiving imaging data. The signal processing apparatus 300 further comprises a processor (CPU) 320 for controlling the apparatus 100, a working memory 330 (e.g. a random-access memory) and an instruction store 340 storing a computer program comprising computer-readable instructions which, when executed by the processor 320, cause the processor 320 to perform the processing operations of the apparatus 100. The instruction store 340 may comprise a ROM (e.g. in the form of an electrically-erasable programmable read-only memory (EEPROM) or flash memory) which is pre-loaded with the computer-readable instructions. Alternatively, the instruction store 340 may comprise a RAM or similar type of memory, and the computer-readable instructions can be input thereto from a computer program product, such as a computer-readable storage medium 350 such as a CD-ROM, etc. or a computer-readable signal 360 carrying the computer-readable instructions.

In the present example embodiment, the combination of the hardware components shown in FIG. 3, comprising the processor 320, the working memory 330 and the instruction store 340, is configured to implement the functionality of the scan parameter obtaining module 110, the conversion factor evaluation module 120, the mapping generator module 140 and the distance calculator module 150 of the apparatus 100, while the working memory 330 or instruction store 340 provide the data storage module 130 of the apparats 100.

Figure 4:
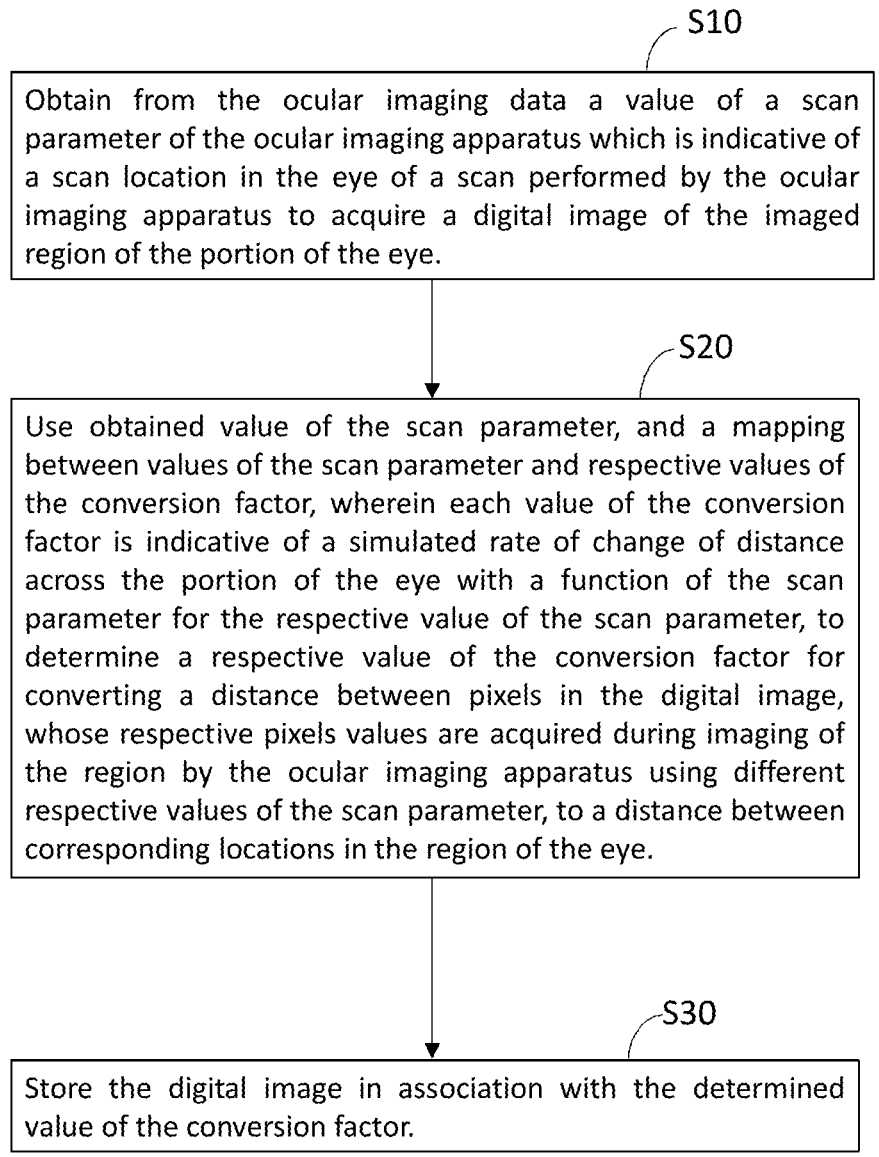
FIG. 4 is a flow diagram illustrating a computer-implemented method of processing ocular imaging data according to the first example embodiment herein.

FIG. 4 is a flow diagram illustrating a computer-implemented method according to the first example embodiment herein, by which the apparatus 100 processes ocular imaging data generated by the controller 205 of the SLO-OCT imaging apparatus 200 to evaluate a conversion factor for calculating a distance between designated ocular features in an imaged region of the retina of the eye 280.

In step S10 of FIG. 4, the scan parameter obtaining module 110 obtains from the ocular imaging data a value of a scan parameter of the ocular imaging apparatus 200 which is indicative of a scan location in the eye 280 of a scan performed by the ocular imaging apparatus 200 to acquire a digital image of the imaged region of the portion of the eye 280. In step S10, the scan parameter obtaining module 110 may, as in the present example embodiment, obtain a first scan parameter value $\theta_c$ and a second scan parameter value $\varphi_c$ that are indicative of a location on the retina of the eye 280 at which an OCT C-scan scan has been performed by the SLO-OCT imaging apparatus 200, by receiving these values as part of the ocular imaging data generated by the SLO-OCT imaging apparatus 200. The ocular imaging data may, as in the present example embodiment, further comprise data characterising other aspects of the image acquisition process by which the SLO-OCT imaging apparatus 200 acquires a digital tomographic image of an imaged region of the retina of the eye 280, for example the ranges of scan parameter values, $\Delta\theta$ and $\Delta\varphi$, covered by the C-scan of the region. It should be noted, however, that the first scan parameter value $\theta_c$ and the second scan parameter value $\varphi_c$ may instead indicate the location on the retina of a C-scan scan that is to be performed by the SLO-OCT imaging apparatus 200; in this case, the conversion factor calculated by the conversion factor evaluation module 120 can be used to convert a distance between pixels in a digital tomographic image that is subsequently acquired by the SLO-OCT imaging apparatus 200 to a distance between corresponding locations in the retina of the eye 280.

A digital image of the imaged portion of the retina of the eye 280 may also be received by the apparatus 100 in step S10. The ocular imaging data, and the digital image which may also be received in step S10, may be provided in any suitable file structure and/or file format known to those versed in the art. For example, in one example implementation, the first scan parameter value $\theta_c$, the second scan parameter value $\varphi_c$, and the ranges of scan parameter values, $\Delta\theta$ and $\Delta\varphi$, covered by the C-scan of the region of the retina (any other items of information defining/characterising the C-scan that may be included in the ocular imaging data) may be provided in a header of a digital image file containing the digital image of the region of the retina, or in a file that is separate from the digital image file and stored in a folder (or a sub-folder) of the digital image file.

In step S20 of FIG. 4, the conversion factor evaluation module 120 uses the obtained value of the scan parameter, and a mapping 125 between values of the scan parameter and respective values of the conversion factor, wherein each value of the conversion factor is indicative of a simulated rate of change of distance across the retina of the eye 280 with a function of the scan parameter for the respective value of the scan parameter, to determine a respective value of the conversion factor for converting a distance between pixels in the digital tomographic image, whose respective pixels values are acquired during imaging of the region by the ocular imaging apparatus 200 for different respective values of the scan parameter, to a distance between corresponding locations in the region of the eye 280. The function of the scan parameter may, as in the present example embodiment, be the identity function so that each value of the conversion factor is indicative of a simulated rate of change of distance across the retina of the eye 280 with the scan parameter for the respective value of the scan parameter. However, the function is not limited to the identity function and may take various other forms, as discussed below.

The conversion factor evaluation module 120 may, as in the present example embodiment, use the values of the first and second scan parameters, $\theta_c$ and $\varphi_c$, obtained in step S10, together with a mapping 125 (which may be obtained using a computer simulation of ray propagation through the SLO-OCT imaging apparatus 200 and the eye 280, as described below) between values of the scan parameters $\theta$ and $\varphi$, and respective values of the conversion factor, to determine, for the received values of the first and second scan parameters, $\theta_c$ and $\varphi_c$: (i) corresponding values of a horizontal conversion factor, $CF_h$, for converting the distance along a horizontal direction in the digital image between the pixels in the received digital C-scan image to the distance in the corresponding direction on the retina between corresponding locations in the imaged region of the retina of the eye 280; and (ii) corresponding values of a vertical conversion factor, $CF_v$, for converting the distance along a vertical direction in the digital image between the pixels in the received digital C-scan image to the distance in the corresponding direction on the retina between corresponding locations in the imaged region of the retina of the eye 280. For a given value of the scan parameter $\theta$, the horizontal conversion factor $CF_h$ is indicative of a simulated rate of change of distance across the retina of the eye 280 with a function (in this example, the identity function) of the scan parameter $\theta$ for the given value of the scan parameter $\theta$. Similarly, for a given value of the scan parameter $\varphi$, the vertical conversion factor $CF_v$ is indicative of a simulated rate of change of distance across the retina of the eye 280 with a function (in this example, the identity function) of scan parameter $\varphi$ for the given value of the scan parameter $\varphi$. It should be noted that, in general, the function of scan parameter $\theta$ may or may not be the same as the function of scan parameter $\varphi$.

In variants of the present example embodiment, in which the scan performed by the SLO-OCT imaging apparatus 200 is an OCT B-scan, the conversion factor evaluation module 120 may use the values of the first and second scan parameters, $\theta_c$ and $\varphi_c$, obtained in step S10, together with a mapping 125 (which may be obtained using a computer simulation of ray propagation through the SLO-OCT imaging apparatus 200 and the eye 280, as described below) between values of the scan parameters $\theta$ and $\varphi$, and respective values of the conversion factor, to determine, for the received values of the first and second scan parameters, $\theta_c$ and $\varphi_c$, a corresponding value of a single conversion factor CF for converting the distance in the A-scan arraying direction (in which A-scans acquired by the SLO-OCT imaging apparatus 200 are arrayed to form the B-scan) between the pixels in the digital B-scan image to the distance in the scan direction on the retina between corresponding locations in the imaged region of the retina of the eye 280.

Figure 5:
FIG. 5 illustrates an example of a mapping between scan parameter values and conversion factor values used in the first example embodiment, in the form of a look-up table.

The mapping 125 may, as in the present example embodiment, take the form of a look-up table 400, which relates values of the scan parameters $\theta$ and $\varphi$ to corresponding values of the horizontal and vertical conversion factors, $CF_h$ and $CF_v$, as illustrated in FIG. 5. The mapping 125 may, however, be provided in an alternative form of a function of the scan parameters $\theta$ and $\varphi$. Furthermore, the mapping 125 may, as in the present example embodiment, relate values of the scan parameter(s), which span a range of scan parameter values covered in a widefield scan of the retina by the SLO-OCT imaging apparatus 200, to respective values of the horizontal and vertical conversion factors $CF_h$ and $CF_v$ (or the respective single conversion factor CF in the variant of the example embodiment mentioned above). The widefield scan may cover at least 50% of the surface of the retina of the eye 280, and more preferably at least 60, 70 or 80% of the surface of the retina.

In step S30 of FIG. 4, the data storage module 130 stores the digital image in association with the value of the horizontal and vertical conversion factors $CF_h$ and $CF_v$ determined in step S20 of FIG. 4 (or the single conversion factor CF that is determined in the described variant), for example using a pointer which links a storage element of the data storage module 130 storing the determined conversion factors to the digital image file.

The data processing operations described above with reference to FIG. 4 are not limited in their applicability to ocular imaging data generated by the controller 205 in relation to the acquisition of OCT C-scans, and is further applicable not only to ocular imaging data generated by the controller 205 in relation to the acquisition of OCT B-scans (as noted above) but also to SLO images and other ocular images representing the results of a one- or two-dimensional scan of the retina or other portion of the eye 280.

Figure 6:
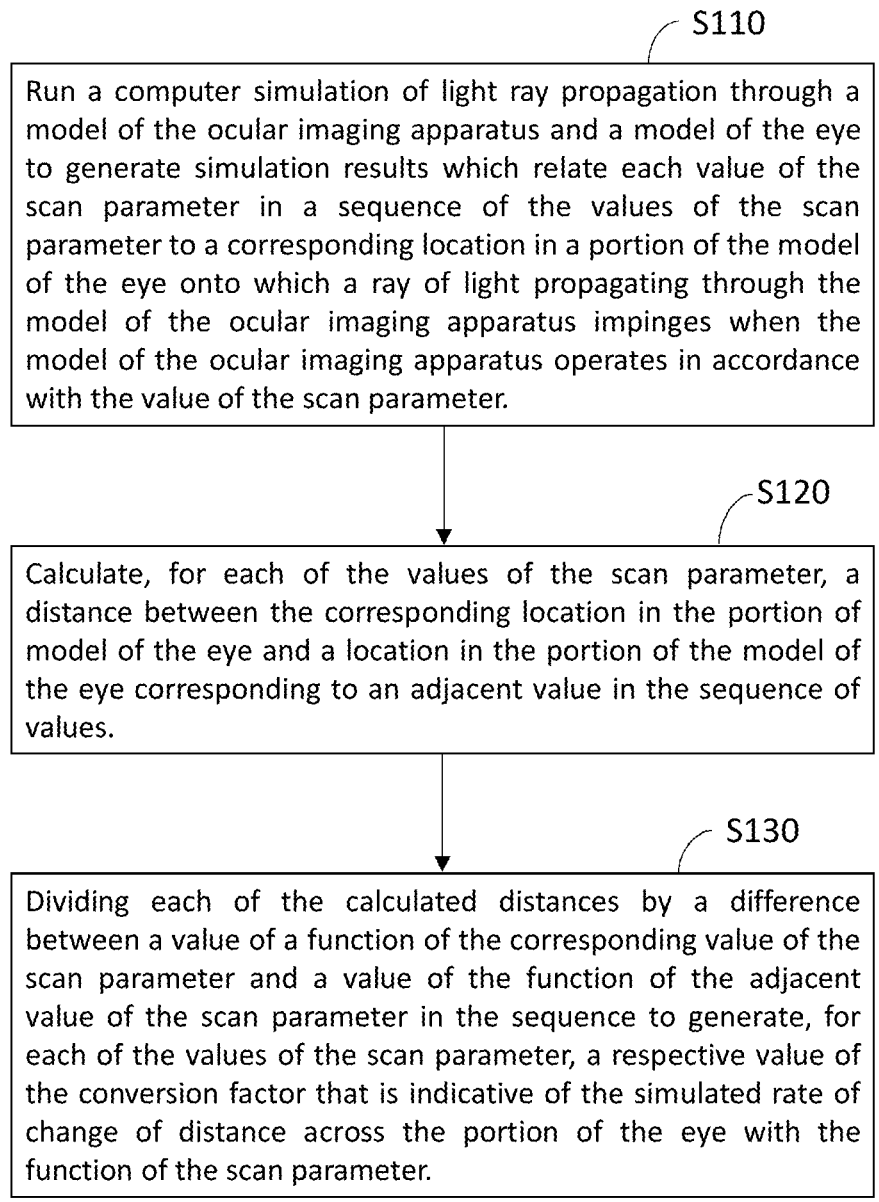
FIG. 6 is flow diagram illustrating a computer-implemented method of generating a mapping between a value of a scan parameter and a value of a conversion factor in accordance with an example embodiment.

FIG. 6 illustrates a general process by which the (optional) mapping generator module 140 of the present example embodiment generates the mapping 125 that is used by the conversion factor evaluation module 120 to determine the conversion factors. The inclusion of the mapping generator module 140 in the apparatus 100 provides the advantage of allowing the mapping 125 to be updated to account for any changes in the optical elements or their arrangement in the SLO-OCT imaging apparatus 200, and/or to tailor the mapping 125 to the eye of the subject that is imaged by the SLO-OCT imaging apparatus 200, for example. The same process may, however, be used during an initial setting up of the SLO-OCT imaging apparatus 200 in the factory to generate the mapping 125 that is subsequently to be used by the conversion factor evaluation module 120.

Referring to FIG. 6, in step S110, the mapping generator module 140 generates the mapping 125 by running a computer simulation of light ray propagation through a model of the SLO-OCT imaging apparatus 200 (or, more generally, any other scanner-based ocular imaging apparatus) and a model of the eye 280 to generate simulation results. The simulation results relate each value of the scan parameter in a sequence of the values of the scan parameter to a corresponding location in the model of the eye 280 onto which a ray of light propagating through the model of the ocular imaging apparatus impinges when the model of the ocular imaging apparatus operates in accordance with the value of the scan parameter.

The computer simulation may, as in the present example embodiment, use measurements of the eye 280 that is to be imaged by the ocular imaging apparatus to model ray propagation through the model of the eye 280 and the model of the ocular imaging apparatus. These measurements may provide information on the size and/or shape of the eye, and may be obtained using ocular imaging techniques such as computerized tomography, ultrasonography and magnetic resonance imaging, for example. This information may improve the accuracy of the model eye and therefore make the simulation results more realistic.

In step S120 of FIG. 6, the mapping generator module 140 calculates, for each of the values of the scan parameter, a distance between the corresponding location in the model of the eye 280 (i.e. the location in the model of the eye 280 onto which a ray of light propagating through the model of the ocular imaging apparatus impinges when the model of the ocular imaging apparatus operates in accordance with the value of the scan parameter) and a location in the model of the eye 280 corresponding to an adjacent value in the sequence of values (i.e. the location in the model of the eye 280 onto which a ray of light propagating through the model of the ocular imaging apparatus impinges when the model of the ocular imaging apparatus operates in accordance with a second value of the scan parameter which is adjacent to the value of the scan parameter, the adjacent value being the next or previous value in the sequence, or next-but-one or previous-but-one value in the sequence, for example).

In step 130 of FIG. 6, the mapping generator module 140 divides each of the calculated distances by a difference between the corresponding value of the function of the value of the scan parameter and a value of the function of the adjacent value of the scan parameter in the sequence to generate, for each of the values of the scan parameter, a respective value of the conversion factor that is indicative of the simulated rate of change of distance across the portion of the eye 280 with a function of the scan parameter. Where the function is the identity function, as in the present example embodiment, in step 130 of FIG. 6, the mapping generator module 140 may divide each of the calculated distances by a difference between the corresponding value of the scan parameter and the adjacent value of the scan parameter in the sequence to generate, for each of the values of the scan parameter, a respective value of the conversion factor that is indicative of the simulated rate of change of distance across the portion of the eye 280 with the scan parameter.

As steps S110, S120 and S130 of FIG. 6 are performed to generate the mapping 125 that is used by step S20 of FIG. 3, steps S110, S120 and S130 are performed by the mapping generator module 140 before step S20 in FIG. 4 is performed by the conversion factor evaluation module 120.

Figures 7A, 7B:
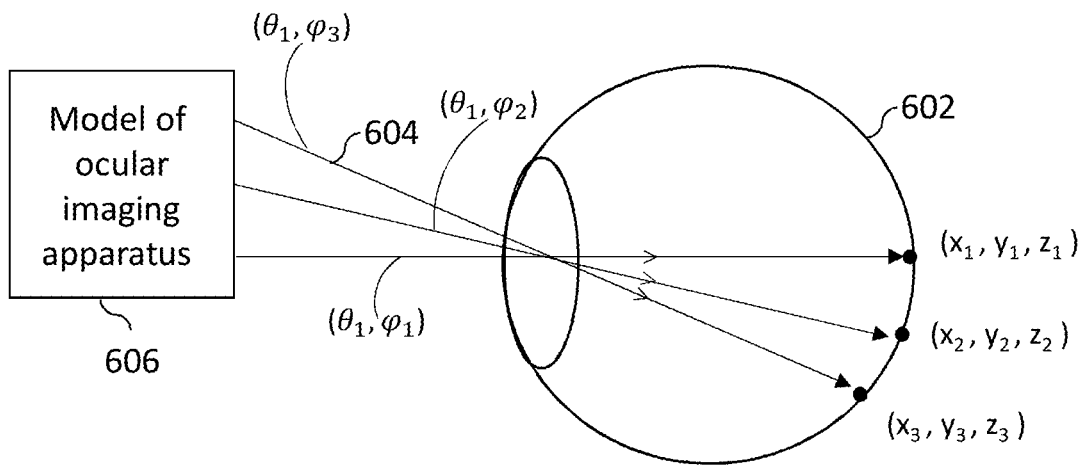
FIG. 7A is a schematic illustration of a computer simulation of ray propagation through a model of an ocular imaging apparatus and a model of an eye.
FIG. 7B illustrates an example of a look-up table, generated based on the computer simulation in 7A, which can be used to derive the mapping between a value of a scan parameter and a value of a conversion factor, in accordance with an example embodiment.

A more detailed example implementation of the process of FIG. 6 will now be described with reference to FIGS. 7A and 7B. In step S110 of FIG. 6, the inclination angle $\theta$ of the H-galvanometer mirror 260 and the inclination angle $\varphi$ of the V-galvanometer mirror 214 may be taken as the first and second scan parameters, respectively, and the computer simulation may be run to trace, for each pair of values of $\theta$ and $\varphi$ of a plurality of different possible combinations of values of $\theta$ and $\varphi$, the propagation of a light beam (ray) 604 through a model 606 of SLO-OCT imaging apparatus 200 onto a position on a model 602 of a retina of the eye 280, as illustrated in FIG. 7A. The simulation results therefore map each pair of values of $\theta$ and $\varphi$ to a corresponding location on the retina model 602 onto which the light beam is incident when the model of the SLO-OCT imaging apparatus 200 operates in accordance with the pair of values of $\theta$ and $\varphi$. The mapping between each pair of values of $\theta$ and $\varphi$, and the corresponding location on the retina model 602 may, as in the present example embodiment, be stored in a table, as illustrated in FIG. 7B.

The plurality of pairs of values of the scan parameters $\theta$ and $\varphi$ may, as in the present example embodiment, correspond to all possible combinations of the values of $\theta$ and $\varphi$ that span respective ('maximum') ranges of $\theta$ and $\varphi$ that are required for the SLO-OCT imaging apparatus 200 to scan substantially the whole retina (e.g. 80% or more of the retina), wherein the difference between adjacent angle values in each of these ranges is the smallest increment by which the respective scanning element (the H-galvanometer mirror 260 or the V-galvanometer mirror 214) can be moved.

However, in some example embodiments, the plurality of pairs of values of $\theta$ and $\varphi$ for which the simulation of light ray propagation is run may instead be a subset of all the possible combinations mentioned above. For example, the combinations of the values of $\theta$ and/or $\varphi$ for which the simulation of light ray propagation is run may span respective ranges of $\theta$ and $\varphi$ that are smaller than the 'maximum' ranges mentioned above (or the range of one of these angles is smaller than the respective 'maximum' range mentioned above).

The mapping generator module 140 may decimate the inclination angle value pairs mentioned above (whether they span the 'maximum' ranges, or at least one of the more limited ranges mentioned above) to create a sparse selection containing only a subset of these inclination angle value pairs. Selecting pairs of $\theta$ and $\varphi$ values in this way is advantageous as storage space is reduced. Furthermore, the simulation results may be interpolated to determine the location of incidence of the light beam 604 on the model retina 602 for intermediate values of θ and φ, for which no simulation has been run.

FIG. 7A provides a schematic illustration of the computer simulation of ray propagation performed in step S110, and illustrates three different light beams emitted by the model 606 of the SLO-OCT imaging apparatus 200, each light beam being emitted when the model 606 of the SLO-OCT imaging apparatus 200 operates in accordance with a respective (different) pair of values for θ and φ. As shown in FIG. 7A, each pair of values of θ and φ results in the respective simulated light beam 604 being incident on the model 602 of the retina at a different location on the retina. In FIG. 7A, each position of these locations is expressed in terms of respective cartesian coordinates (x, y, z).

FIG. 7B illustrates a two-dimensional table 600, which relates each pair of values of θ and φ to a corresponding set of coordinates identifying the corresponding location on the retina model 602 at which the light beam 604 is incident on the retina model 602 when the model 606 of the SLO-OCT imaging apparatus 200 operates in accordance with the pair of values for θ and φ. As shown in FIG. 7B, the pairs of values of θ and φ may be arranged in the two-dimensional table 600, with each row containing different values of φ running from $\varphi_1$ to $\varphi_n$, and each column containing different values of θ running from $\theta_1$ to $\theta_m$, where m and n are integers which may or may not be equal. Each cell 610 in table 600 stores a position (x, y, z) on the retina model 602 which has been calculated for the values of θ and φ corresponding to that cell 610.

As an implementation of step S120 of FIG. 6, the mapping generator module 140 may first determine, for each cell 610 of the table 600, a respective vertical angle conversion factor, $CF_v$, which is indicative of a simulated rate of change of distance across the retina with changing values of φ. For this purpose, mapping generator module 140 may determine, for each cell 610 in the table 600, the distance between the location on the retina model 602 indicated by the coordinate values (x, y, z) in the cell 610, and the location on the retina model 602 indicated by the coordinate values (x, y, z) in the cell having the same θ value but an adjacent φ value. The word "adjacent" in this context refers to a φ value that is the next highest or next lowest (or next highest/lowest one) in the row as compared to the value of φ of the cell 610. For instance, let $(\theta_i, \varphi_j)$, where i=1, ... m, j=1, ... n denote a plurality of pairs of values for (θ, φ), each having a corresponding cell 610 in the table 600 that stores corresponding location coordinates (x, y, z). Step S120 of FIG. 6 therefore implements the calculation of the distance between the respective (x, y, z) values of $(\theta_i, \varphi_j)$ and $(\theta_i, \varphi_{j+1})$ for all values of $(\theta_i, \varphi_j)$, i=1, ... m, j=1, ... n, in the table 600. For convenience, in the present example, the (x, y, z) point corresponding to $(\theta_i, \varphi_j)$ is denoted herein as $r_{\theta_i,\varphi_j}$.

By way of an example, in FIG. 7B, the mapping generator module 140 calculates the distance between the points $(x_1, y_1, z_1)$ and $(x_2, y_2, z_2)$ on the retina model 602 corresponding to (θ, φ) values of $(\theta_1, \varphi_1)$ and $(\theta_1, \varphi_2)$, respectively. This distance may, as in the present example embodiment, be calculated using Pythagoras' theorem in three-dimensional Euclidean space:

$$d((x_1,y_1,z_1),(x_2,y_2,z_2)) = \sqrt{(x_1-x_2)^2+(y_1-y_2)^2+(z_1-z_2)^2}$$

In the present example, the above-calculated distance is stored in association with the cell 610 corresponding to the value pair $(\theta_1, \varphi_1)$. In other words, for each pair of values $(\theta_i, \varphi_j)$ in the table 600, the calculated distance between the respective (x, y, z) values calculated for angle value pair $(\theta_i, \varphi_j)$ and angle value pair $(\theta_i, \varphi_{j+1})$ may be stored in the cell 610 of the table 600 corresponding to $(\theta_i, \varphi_j)$, as $d(r_{\theta_i,\varphi_j}, r_{\theta_i,\varphi_{j+1}})$.

In step S130 of FIG. 6, the mapping generator module 140 also calculates, for each cell 610 corresponds to can parameter values $(\theta_i, \varphi_j)$, a value of $\varphi_{j+1}-\varphi_j$. The mapping generator module 140 further divides the calculated distance $d(r_{\theta_i,\varphi_j}, r_{\theta_i,\varphi_{j+1}})$ for each cell 610 by the corresponding value of $\varphi_{j+1}-\varphi_j$, in order to generate the vertical angle conversion factor $CF_v$ for that cell 610, which is indicative of a simulated rate of change of distance across the retina with φ for the location on the retina indicated by the θ and φ values of the cell 610.

In the present example embodiment, the mapping generator module 140 further determines a horizontal angle conversion factor $CF_h$ for each pair of (θ, φ) values that is indicative of a simulated rate of change of distance across a portion of the retina with θ. For this purpose, the mapping generator module 140 may additionally perform, in step S120 of FIG. 6, the calculation of the distance between the respective (x, y, z) values of $(\theta_i, \varphi_j)$ and $(\theta_{i+1}, \varphi_j)$ for all values of $(\theta_i, \varphi_j)$ in the table. In the example in FIG. 6B, the calculated distance is stored against each entry $(\theta_i, \varphi_j)$ as $d(r_{\theta_i,\varphi_j}, r_{\theta_{i+1},\varphi_j})$.

Furthermore, in step S130, the mapping generator module 140 further calculates, for each cell in the table 600 corresponding to a respective angle value pair $(\theta_i, \varphi_j)$, the value $\theta_{i+1}-\theta_i$. The mapping generator module 140 further divides the stored calculated distance $d(r_{\theta_i,\varphi_j}, r_{\theta_{i+1},\varphi_j})$ for each cell corresponding to $(\theta_i, \varphi_j)$ by the corresponding value of $\theta_{i+1}-\theta_i$, in order to generate the horizontal angle conversion factor $CF_h$ that is indicative of a simulated rate of change of distance across the portion the retina with θ.

In the present example embodiment, the conversion factor is indicative of a simulated rate of change of distance across a portion of the eye with respect to the scan parameter, with the function in Step 20 being the identity function. The mapping generator module 140 therefore determines a horizontal angle conversion factor $CF_h$ for each of the pairs of θ and φ values that is indicative of a simulated rate of change of distance across a portion of the retina with θ, and further determines the vertical angle conversion factor $CF_v$ for each of the pairs of θ and φ values that is indicative of a simulated rate of change of distance across a portion of the retina with φ. However, in an alternative example embodiment, the function in Step 20 may not be the identity function but may, for example, be a function which correlates changes in the scan parameter to changes in another parameter such as an angle of the light beam scanned by the ocular imaging apparatus, for example.

In some example embodiments, the conversion factor may be indicative of a simulated rate of change of distance across the portion of the eye with respect to an external angle of the light beam in the simulation, which is determined by an inclination angle of a galvanometer mirror in the model 606 of the ocular imaging apparatus that is rotated to perform a scan in the simulation. This external angle may be an angle between a simulated light beam 604 entering the model 602 of the eye and a reference direction of the model eye 602 (e.g. an optical axis of the lens of the model eye 602) in the computer simulation of Step S110. However, the external angle need not to be defined by respect to the model eye 602, and may instead be defined with respect of a reference direction or plane of the model 606 of the ocular imaging apparatus, for example.

Figure 8:
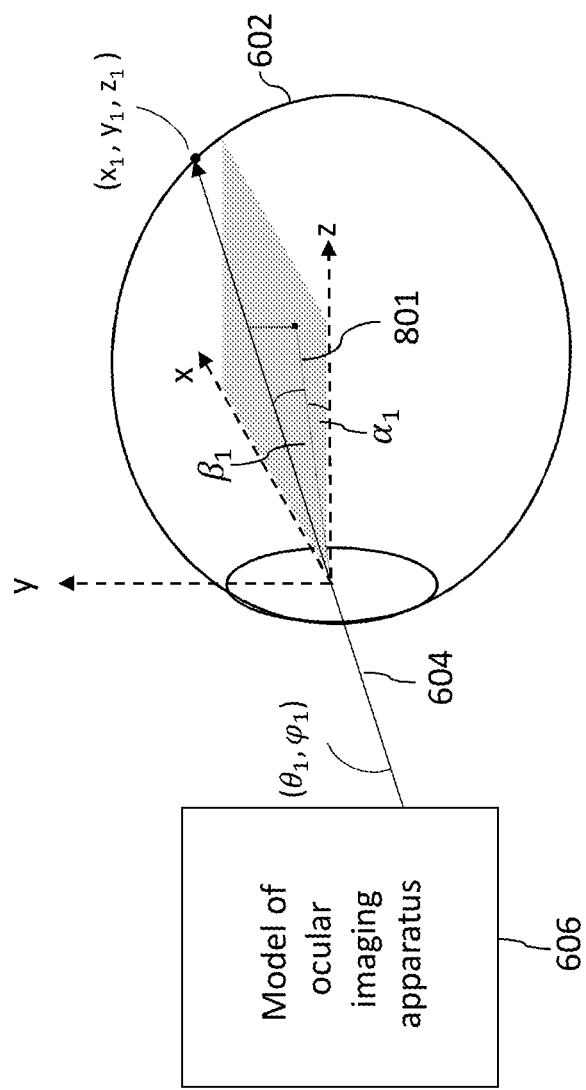
FIG. 8 is a schematic illustration of ray propagation through a model of an ocular imaging apparatus and a model of an eye.

FIG. 8 illustrates light ray propagation through the model 606 of the ocular imaging apparatus and the model 602 of the eye in the computer simulation, wherein the external angle is an azimuth angle α or an elevation angle β of the simulated light beam 604 relative to an optical axis of the ocular lens in the model eye 602. In FIG. 8, the optical axis of the lens is taken to be the z-axis. The azimuth angle α of the incident light beam 604 may be defined as the angle between the optical axis of the lens of the eye 602 and a projection 801 of a vector representing the incident light beam 604 onto the horizontal (x-z) plane. The elevation angle may be defined as the angle between the incident light beam 604 and the projection 801 of vector representing the incident light beam 604 onto the horizontal plane. Referring to the ocular imaging system of FIG. 2, the azimuth angle α may either be a linear or non-linear function of the inclination angle θ of the H-galvanometer mirror. Similarly, the elevation angle β may be a linear or non-linear function of the inclination angle φ of the V-galvanometer mirror. Furthermore, α may also be a function of φ, while β may also be a function of θ. Together, the azimuth angle α and the elevation angle β of the incident light beam 604 therefore define the location of the eye 602 in the model at which the light beam 604 scanned by the ocular imaging system 606 impinges.

As an example, in a variant of the first example embodiment, the mapping generator module may generate a mapping between inclination angle pair (θ, φ) and a horizontal angle conversion factor $CF_h'$ that is indicative of a simulated rate of change of distance across the portion the retina with azimuth angle α. Furthermore, the mapping generator module of the variant may also generate a mapping between inclination angle pair (θ, φ) and a vertical angle conversion factor $CF_v'$ that is indicative of a simulated rate of change of distance across the portion the retina with elevation angle β (as defined above).

The mapping generator module of the variant may generate the mapping that is used by the conversion factor evaluation module 120 to determine the conversion factors in a similar way to the first example embodiment. More particularly, the mapping generator module of the variant may perform the same processes as the example embodiment in Step S110 of FIG. 6, namely selecting a plurality of pairs of values for (θ, φ) and running a computer simulation to calculate, for each pair of values of (θ, φ), a corresponding location (x, y, z) on the retina. Furthermore, the mapping between values of (θ, φ) and corresponding locations (x, y, z) may be provided in the form of a table, as described above with reference to FIG. 7B. The process of step S120 in FIG. 6 may also be performed in the way as in the example embodiment.

However, the present variant differs from the example embodiment by the process performed in Step 130. In the example embodiment (wherein values of conversion factors $CF_h$, and $CF_v$ as calculated), the distance on the retina between points corresponding to adjacent pairs of (θ, φ) values is divided by the difference in the θ value between the adjacent pairs (to generate the horizontal angle conversion factor $CF_h$) or by the difference in the φ value between the adjacent pairs (to generate the vertical angle conversion factor $CF_v$). However, in the variant, because the conversion factor represents a rate of change of distance across the retina with respect to the azimuth angle α or the elevation angle β, the mapping generator module of the variant performs an additional step of deriving, for each pair of (θ, φ) values in the plurality of selected pairs of (θ, φ) values, a corresponding pair of values for (α, β). To derive a pair of corresponding (α, β) values from a pair of (θ, φ) values, the mapping generator module of the variant may first perform a computer simulation to determine a unit vector (L, M, N) corresponding to the pair of (θ, φ) values, the unit vector representing (in cartesian coordinates) the simulated incident light beam 604 scanned into the model eye 602 by the ocular imaging system when the inclination angles of its horizontal and vertical galvanometer mirrors are set in accordance with the (θ, φ) values. The mapping generator module of the variant may further convert each unit vector (L, M, N) from cartesian coordinates to spherical coordinates to obtain the (θ, φ) values that represent the azimuth angle θ and the elevation angle φ corresponding to the unit vector.

After obtaining the (α, β) values corresponding each pair of (θ, φ) values in the plurality of selected pairs of (θ, φ) values, the mapping generator module of the variant may calculate, for each pair of (θ, φ) values, the difference between the α value of the (θ, φ) pair and the α value of a (θ, φ) pair having the same φ value but the next highest or the next lowest θ value in the plurality of selected (θ, φ) pairs.

As an example, referring back to table 600 in FIG. 7B, in which each cell 610 corresponds to a pair of (θ, φ) values, the mapping generator of the variant may calculate a corresponding pair of ($α_i$, $β_j$) values for each ($θ_i$, $φ_j$) pair in the table 600, wherein i=1, . . . m, j=1, . . . n. The mapping generator module of the variant may further calculate, in a modified step 130, for each cell 610 in the table 600 corresponding to a respective angle value pair ($θ_i$, $φ_j$), the value $α_{i+1} - α_i$, wherein $α_{i+1}$ is the azimuth angle α corresponding to ($θ_{i+1}$, $φ_j$).

The mapping generator module of the variant may further divide the distance $d(r_{θ_i,φ_j}, r_{θ_{i+1},φ_j})$ calculated in a modified step 120 (namely, the distance between the respective (x, y, z) values of ($θ_{i+1}$, $φ_j$) and ($θ_i$, $φ_j$)) for each ($θ_i$, $φ_j$) pair (i=1, . . . m, j=1, . . . n) by the corresponding value of $α_{i+1} - α_i$, in order to generate a horizontal angle conversion factor $CF_h'$ that is indicative of a simulated rate of change of distance across the portion the retina with azimuth angle α. By calculating $CF_h'$ for every pair of (θ, φ) values in the plurality of the selected (θ, φ) pairs, a mapping between (θ, φ) and $CF_h'$ can be established for the desired range of inclination angles.

In addition, in the modified Step S130, the mapping generator module of the variant may further calculate, for each cell in the table 600 corresponding to a respective angle value pair ($θ_i$, $φ_j$), the value $β_{j+1} - β_j$, wherein $β_{j+1}$ is the elevation angle β corresponding to ($θ_i$, $φ_{j+1}$). The mapping generator module of the variant may further divide the calculated distance $d(r_{θ_i,φ_j}, r_{θ_i,φ_{j+1}})$ (namely, the distance between the respective (x, y, z) values of ($θ_i$, $φ_j$) and ($θ_i$, $φ_{j+1}$) as obtained in modified Step S120) for each ($θ_i$, $φ_j$) pair by the corresponding value of $β_{j+1} - β_j$, in order to generate a vertical conversion factor $CF_v'$ that is indicative of a simulated rate of change of distance across the portion the retina with elevation angle β. By performing this calculation for all ($θ_i$, $φ_j$) pairs in the selected plurality of ($θ_i$, $φ_j$) pairs (i=1, . . . m, j=1, . . . n), a mapping between (θ, φ) and a corresponding vertical conversion factor $CF_v'$ can be established.

Figure 9B:
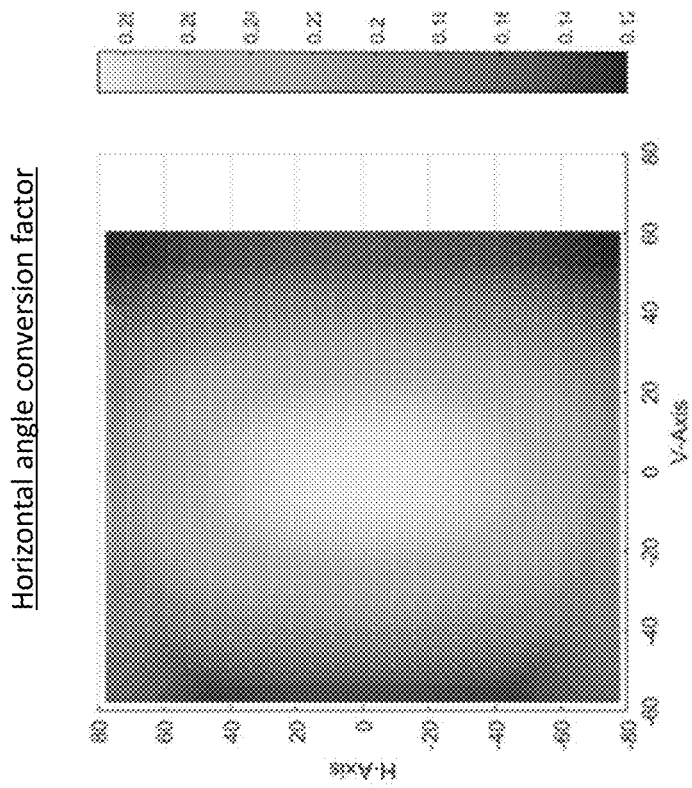
FIG. 9B is a grey-scale plot of the calculated horizontal angle conversion factor as a function of H-galvanometer mirror inclination angle $\theta$ and V-galvanometer mirror inclination angle $\varphi$.
Figure 9A:
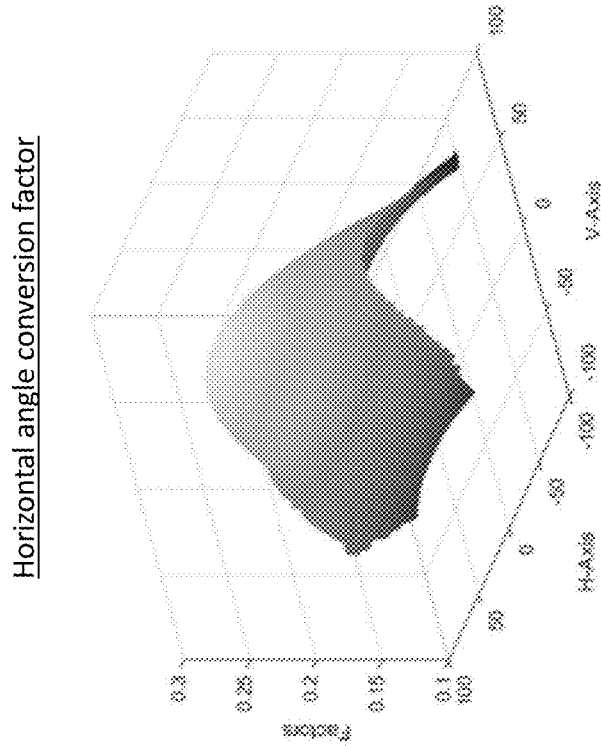
FIG. 9A is a three-dimensional plot of a calculated horizontal angle conversion factor as a function of H-galvanometer mirror inclination angle $\theta$ and V-galvanometer mirror inclination angle $\varphi$.

FIG. 9A shows a three-dimensional plot of the calculated horizontal angle conversion factor $CF_h'$ as a function of H-galvanometer mirror inclination angle θ and V-galvanometer mirror inclination angle φ. FIG. 9B is a grey-scale representation of the calculation results shown in FIG. 9A.

Figure 10B:
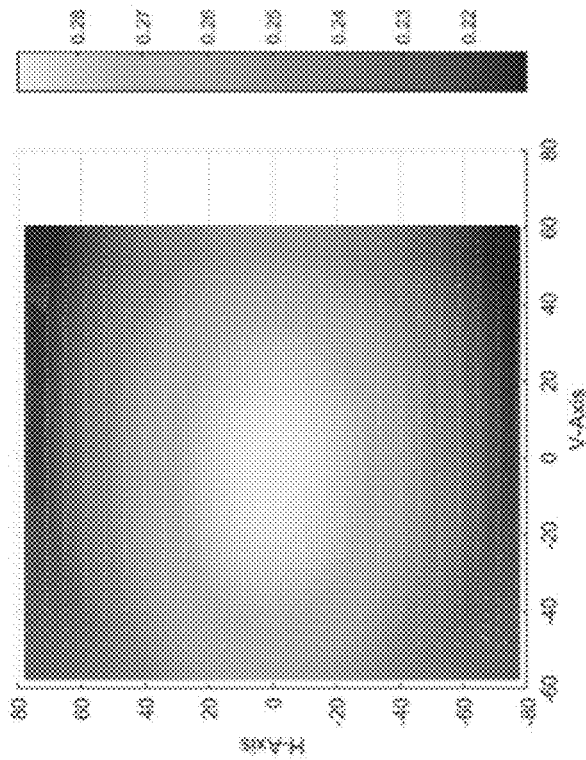
FIG. 10B is a grey-scale plot of the calculated vertical angle conversion factor as a function of H-galvanometer mirror inclination angle $\theta$ and V-galvanometer mirror inclination angle $\varphi$.
Figure 10A:
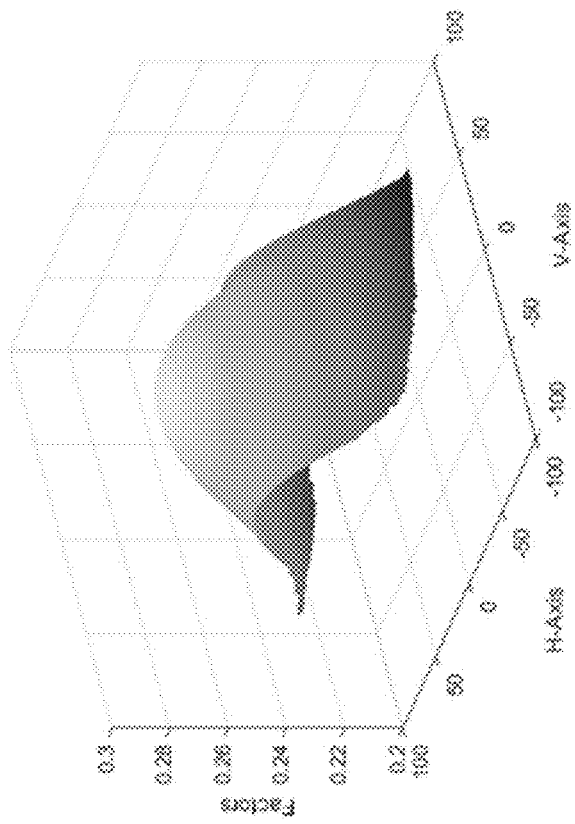
FIG. 10A is a three-dimensional plot of a calculated vertical angle conversion factor as a function of H-galvanometer mirror inclination angle $\theta$ and V-galvanometer mirror inclination angle $\varphi$.

FIG. 10A shows a three-dimensional plot of the calculated vertical angle conversion factor $CF_v'$ as a function of H-galvanometer mirror inclination angle θ and V-galvanometer mirror inclination angle φ. FIG. 10B is a grey-scale representation of the calculation results shown in FIG. 10A.

It should be understood that, although the example of FIGS. 7A and 7B employs two scan parameters and therefore uses two corresponding sets of mappings, apparatus 100 may similarly work with only one scan parameter. For example, for an OCT B-scan obtained by varying only V-galvanometer mirror inclination angle φ, the mapping generator module 140 only needs to calculate a vertical angle conversion factor for φ. This vertical angle conversion factor could then be used to convert a distance in a first direction (e.g. vertical direction) between pixels in the generated OCT digital image into a distance in a corresponding direction (e.g. vertical direction) between corresponding locations on the surface of the retina.

Figure 11:
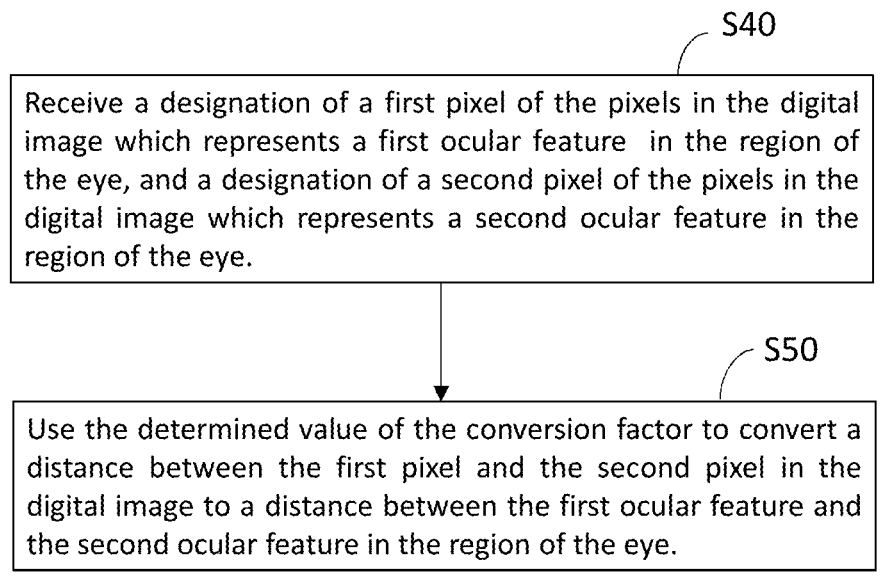
FIG. 11 is a flow diagram illustrating a computer-implemented method of calculating a distance between designated ocular features in the imaged region of the eye using a value of a conversion factor in accordance with an example embodiment.

FIG. 11 is a flow diagram illustrating a process by which the (optional) distance calculator module 150 of the apparatus 100 determines a distance between designated ocular features in the imaged region of the eye 280, by using the value of the conversion factor determined in step S30 of FIG. 3 to convert a distance between two pixels in the digital image acquired in step S10 to a physical distance between corresponding ocular features in the images region of the eye 280 that is shown in the digital image.

In step S40 of FIG. 11, the distance calculator module 150 receives a designation of a first pixel of the pixels in the digital image which represents a first ocular feature in the imaged region of the retina (or another imaged portion of the eye 280). The distance calculator module 150 further receives a designation of a second pixel of the pixels in the digital image which represents a second ocular feature in the imaged region. It should be noted that each of the first and second ocular feature may be related to any part of the retina in the imaged region of the retina.

The designations of the first pixel and the second pixel may, as in the present example embodiment, be made by a user viewing the digital image on a screen, who can use an input device such as a computer keyboard or mouse, for example, to designate features of interest in the digital image using a cursor on the screen and the like. However, the designation may alternatively be performed by image processing software, such as software running a pattern recognition algorithm which automatically designates points of interest in the digital image. The coordinates of the designated pixels in the digital image are then used for the distance calculation.

More particularly, in step S50 of FIG. 11, the distance calculator module 150 uses the value of the conversion factor determined in step S20 of FIG. 4 to convert a distance between the first pixel and the second pixel in the digital image to a physical distance (i.e. a distance in length units, e.g. metric units such as millimetres) between the first ocular feature and the second ocular feature in the imaged region of the eye 280.

Figure 12:
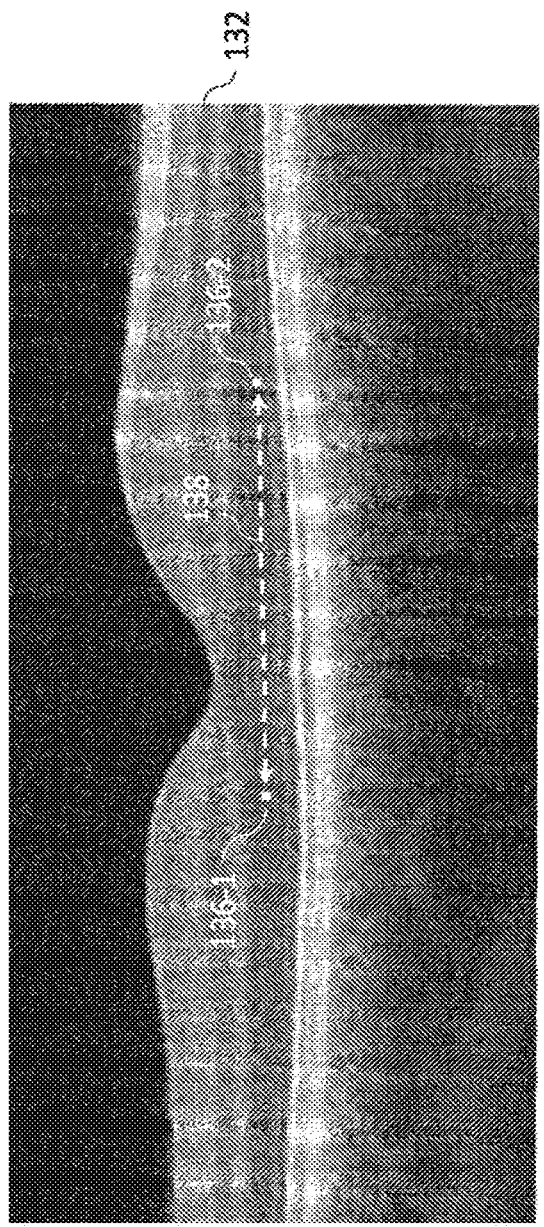
FIG. 12 illustrates an OCT B-scan image having two designated pixels that correspond to designated ocular features in the imaged region of the eye.

As an example, FIG. 12 illustrates a digital image 132 in the form of an OCT B-scan image of a retina, which includes a first pixel 136-1 and a second pixel 136-2 which have been designated by a user, as described above. The distance 138 between the designated pixels 136-1 and 136-2 is converted by the distance calculator module 150 into a distance between the corresponding ocular features in the retina, which may be displayed on the screen to the user.

Where the OCT image is an OCT B-scan generated by varying V-galvanometer mirror 214 inclination angle φ over a predetermined range, for example, the B-scan has an x-dimension corresponding to the scanning direction of the V-galvanometer mirror 214, and a y-dimension corresponding to the depth direction of the eye 280. In this case, by using the vertical angle conversion factor $CF_v$ or $CF_v'$ explained in relation to the example in FIG. 7B, a distance along the x-dimension between any two pixels in the OCT B-scan image can be converted into a physical distance between two corresponding features on the retina.

More specifically, the distance calculator module 150 may first determine the distance in pixels between the first designated pixel and second designated pixel. The distance calculator 150 may further determine a change δφ of the V-galvanometer mirror 214 inclination angle φ that corresponds to the determined pixel distance. More specifically, the angle δφ is the angle through which the V-galvanometer mirror 214 has been (or is to be) rotated in order to generate pixel data for the determined pixel distance between the first and second designated pixels. This angular change δφ may be calculated based on the sampling rate of the OCT photodetector and the angular speed of the V-galvanometer mirror, for example.

When the vertical conversion factor is indicative of a rate of change of distance with the inclination angle φ of the V-galvanometer mirror, the distance calculator module 150 may thus calculate the real (physical) distance between the retina features corresponding to the two designated pixels by multiplying the value of the vertical angle conversion factor $C_v$, which is applicable to the OCT B-scan image being processed, by the determined angular change δφ. As explained in relation to FIG. 4, the vertical conversion factor $CF_v$ may be determined in step S20 of FIG. 4 by the conversion factor evaluation module 120 based on a value of φ that is received by the scan parameter obtaining module 110 in step S10, i.e. $φ_c$.

Although the above example relates to an OCT B-scan image which is generated by rotating V-galvanometer mirror 214, it should be apparent that the OCT B-scan image may be similarly generated by varying the H-galvanometer mirror 260 inclination angle θ, in which case the OCT B-scan image would have an x-dimension corresponding to the scanning direction of the H-galvanometer mirror 260. In such a scenario, the horizontal angle conversion factor $CF_h$ explained in relation to the example in FIG. 7B can be used to convert a distance along the x-dimension between any two pixels in the OCT B-scan image into a physical distance between two corresponding features on the retina.

In the above examples only one of the V-galvanometer mirror 214 and the H-galvanometer mirror 260 is rotated to acquire a B-scan. In cases where the SLO-OCT imaging system 200 captures an OCT C-scan by varying the inclination angles of both the H-galvanometer mirror 260 and the V-galvanometer mirror 214, the OCT C-scan image may have a first dimension (e.g. a x-dimension) corresponding to the scanning direction of the H-galvanometer mirror 260, a second dimension (e.g. a y-dimension) corresponding to the scanning direction of the V-galvanometer mirror 214, and a third direction (e.g. a z-dimension) corresponding to the depth direction of the eye 280. For an OCT image slice of the OCT C-scan that has only the first and second dimensions (namely, x-dimension and the y-dimension), the distance calculator module 150 may convert a distance between two designated pixels in the C-scan image slice to a physical distance between corresponding retina features in the eye 280. In particular, if the first designated pixel and the second designated pixel are offset relative to each other both in the x-dimension and the y-dimension, then the distance calculator module 150 may use both the horizontal angle conversion factor $CF_h$ and the vertical angle conversion factor $CF_v$ to calculate the physical distance between the respective retina features that correspond with the two designated pixels.

As an example, if the first designated pixel and the second designated pixel are spaced apart by a pixels along the x-dimension of the OCT image slice and spaced part by b pixels along the y-dimension of the OCT image slice, then the distance calculator module 150 may determine an angle $\delta\theta$ of the H-galvanometer mirror 260 that corresponds to the distance a, and further determines an angle $\delta\varphi$ of the V-galvanometer mirror 214 that corresponds to the distance b. The angle $\delta\theta$ is the angle through which the H-galvanometer mirror 260 is required to rotate in order to generate pixel data for the pixel distance a in the x-dimension of the OCT image slice. Similarly, angle $\delta\varphi$ is the angle through which the V-galvanometer mirror is required to rotate in order to generate pixel data for the pixel distance b in the y-dimension of the OCT image slice. The values of $\delta\theta$ and $\delta\varphi$ may be calculated based on the sampling rate of the OCT photodetector and the known angular speeds of the H-galvanometer and V-galvanometer mirrors, for example, or they may be calculated as $a/A \cdot \Delta\theta$ and $b/B \cdot \Delta\varphi$, respectively, in case the scan parameter obtaining module 110 receives the ranges $\Delta\theta$ and $\Delta\varphi$ mentioned above as part of the imaging data, where the digital OCT image slice is composed of an array of A×B pixels.

Upon obtaining $\delta\theta$ and $\delta\varphi$, the distance calculator module 150 may multiply $\delta\theta$ by the horizontal angle conversion factor $CF_h$ obtained in step S30 to calculate a first physical distance along a first direction (e.g. the horizontal direction) between the retina features corresponding to the two designated pixels. The distance calculator module 150 may further multiply $\delta\varphi$ by the vertical angle conversion factor $CF_v$ also obtained in step S30 to calculate a second physical distance along a second direction (e.g. the vertical direction direction) between the retinal features corresponding to the two designated pixels. Finally, the distance calculator module 150 may determine the distance between the first retinal feature (corresponding to the first designated pixel) and the second retinal feature (corresponding to the second designated pixel) by using the first physical distance and the second physical distance. For example, where the first direction corresponding to the first physical distance is substantially orthogonal to the second direction corresponding to the second physical distance, the distance calculator module 150 may calculate the distance between the two retinal features by applying Pythagoras' theorem to the calculated first and second physical distances. This calculated distance may further be output by the apparatus 100. For example, the apparatus 100 may control a computer screen or other visual display unit to display the calculated distance to a user.

It should be noted that when the conversion factor is indicative of a rate of change of distance with respect to a function of the scan parameter other than the identity function, then the change in scan parameter corresponding to the determined pixel distance (between the two designated pixels) is first converted into a corresponding change in the value of the function of the scan parameter. The conversion factor (indicating a rate of change of distance with respect to a function of the scan parameter) can then be multiplied with the corresponding change in the value of the function of the scan parameter, in order to obtain the physical distance in the eye 280 which corresponds to the distance between the designated pixels in the digital image.

There has been described in the foregoing, in accordance with example embodiments herein, an apparatus as set out in E1 to E7 below, and a computer-implemented method as set out in E8 to E14 below, and a computer program as set out in E15 below.

E1. An apparatus 100 for processing ocular imaging data generated by a controller 205 of an ocular imaging apparatus 200 to evaluate a conversion factor for calculating a distance between designated ocular features in an imaged region of a portion of an eye (280), the apparatus comprising:
a scan parameter obtaining module 110 configured to obtain from the ocular imaging data a value of a scan parameter ($\theta$, $\varphi$) of the ocular imaging apparatus (200) which is indicative of a scan location in the eye (280) of a scan performed by the ocular imaging apparatus (200) to acquire a digital image of the imaged region of the portion of the eye (280);
a conversion factor evaluation module (120) configured to use the obtained value of the scan parameter ($\theta$, $\varphi$), and a mapping (125) between values of the scan parameter ($\theta$, $\varphi$) and respective values of the conversion factor ($CF_h$, $CF_v$), wherein each value of the conversion factor is indicative of a simulated rate of change of distance across the portion of the eye (280) with a function of the scan parameter ($\theta$, $\varphi$) for the respective value of the scan parameter ($\theta$, $\varphi$), to determine a respective value of the conversion factor ($CF_h$, $CF_v$) for converting a distance between pixels in the digital image, whose respective pixels values are acquired during imaging of the region by the ocular imaging apparatus (200) using different respective values of the scan parameter ($\theta$, $\varphi$), to a distance between corresponding locations in the region of the eye (280); and
a data storage module (130) configured to store the digital image (132) in association with the determined value of the conversion factor ($CF_h$, $CF_v$).

E2. The apparatus (100) according to E1, further comprising a mapping generator module (140) configured to generate the mapping by:
running a computer simulation of light ray propagation through a model of the ocular imaging apparatus (200) and a model of the eye (280) to generate simulation results which relate each value of the scan parameter ($\theta$, $\varphi$) in a sequence of the values of the scan parameter to a corresponding location in a portion of the model of the eye (280) onto which a ray of light propagating through the model of the ocular imaging apparatus (200) impinges when the model of the ocular imaging apparatus (200) operates in accordance with the value of the scan parameter;
calculating, for each of the values of the scan parameter ($\theta$, $\varphi$), a distance between the corresponding location in the portion of the model of the eye (280) and a location in the portion of the model of the eye (280) corresponding to an adjacent value in the sequence of values; and
dividing each of the calculated distances by a difference between the corresponding value of a function of the value the scan parameter ($\theta$, $\varphi$) and a value of the function of the adjacent value of the scan parameter ($\theta$, $\varphi$) in the sequence to generate, for each of the values of the scan parameter ($\theta$, $\varphi$), a respective value of the conversion factor ($CF_h$, $CF_v$) that is indicative of the simulated rate of change of distance across the portion of the eye (280) with the function of the scan parameter ($\theta$, $\varphi$).

E3. The apparatus (100) according to E2, wherein the mapping generator module (140) is configured to use biological measurements of the eye (280) to model light ray propagation through the model of the eye (280) and the model of the ocular imaging apparatus (200) in the computer simulation.

E4. The apparatus (100) according to any of E1 to E3, further comprising a distance calculator module (150) configured to determine a distance between the designated ocular features in the imaged region of the eye (280) by:
  receiving a designation of a first pixel (136-1) of the pixels in the digital image (132) which represents a first ocular feature in the region of the eye (280), and a designation of a second pixel (136-2) of the pixels in the digital image (132) which represents a second ocular feature in the region of the eye (280); and
  using the determined value of the conversion factor ($CF_h$, $CF_v$) to convert a distance (138) between the first pixel (136-1) and the second pixel (136-2) in the digital image (132) to a distance between the first ocular feature and the second ocular feature in the region of the eye (280).

E5. The apparatus (100) according to any of E1 to E4, wherein the portion of the eye (280) comprises a retina of the eye (280).

E6. The apparatus (100) according to E5, wherein the mapping (125) relates values of the scan parameter, which span a range of scan parameter values covered in a wide-field scan of the retina by the ocular imaging apparatus (200), to respective values of the conversion factor ($CF_h$, $CF_v$).

E7. The apparatus (100) according to any of E1 to E6, wherein
  the apparatus (100) is configured to process, as the ocular imaging data, ophthalmic optical coherence tomography, OCT, imaging data generated by a controller (205) of an OCT imaging apparatus, and
  the scan parameter obtaining module (110) is configured to obtain from the OCT imaging data a value of a scan parameter ($\theta$, $\varphi$) of the OCT imaging apparatus which is indicative of an OCT scan location in the eye (280) of an OCT scan performed by the OCT imaging apparatus to acquire a digital OCT image of the imaged region of the portion of the eye (280).

E8. A computer-implemented method of processing ocular imaging data generated by a controller (205) of an ocular imaging apparatus (200) to evaluate a conversion factor ($CF_h$, $CF_v$) for calculating a distance between designated ocular features in an imaged region of a portion of an eye (280), the method comprising:
  obtaining (S10) from the ocular imaging data a value of a scan parameter ($\theta$, $\varphi$) of the ocular imaging apparatus (200) which is indicative of a scan location in the eye (280) of a scan performed by the ocular imaging apparatus (200) to acquire a digital image of the imaged region of the portion of the eye (280);
  using (S20) the obtained value of the scan parameter ($\theta$, $\varphi$), and a mapping (125) between values of the scan parameter ($\theta$, $\varphi$) and respective values of the conversion factor, wherein each value of the conversion factor ($CF_h$, $CF_v$) is indicative of a simulated rate of change of distance across the portion of the eye (280) with a function of the scan parameter ($\theta$, $\varphi$) for the respective value of the scan parameter ($\theta$, $\varphi$), to determine a respective value of the conversion factor ($CF_h$, $CF_v$) for converting a distance (138) between pixels in the digital image (132), whose respective pixels values are acquired during imaging of the region by the ocular imaging apparatus (200) using different respective values of the scan parameter ($\theta$, $\varphi$), to a distance between corresponding locations in the region of the eye (280); and
  storing (S30) the digital image in association with the determined value of the conversion factor ($CF_h$, $CF_v$).

E9. The computer-implemented method according to E8, further comprising generating the mapping by:
  running (S110) a computer simulation of light ray propagation through a model of the ocular imaging apparatus (200) and a model of the eye (280) to generate simulation results which relate each value of the scan parameter ($\theta$, $\varphi$) in a sequence of the values of the scan parameter ($\theta$, $\varphi$) to a corresponding location in a portion of the model of the eye (280) onto which a ray of light propagating through the model of the ocular imaging apparatus (200) impinges when the model of the ocular imaging apparatus (200) operates in accordance with the value of the scan parameter ($\theta$, $\varphi$);
  calculating (S120), for each of the values of the scan parameter ($\theta$, $\varphi$), a distance between the corresponding location in the portion of model of the eye (280) and a location in the portion of the model of the eye (280) corresponding to an adjacent value in the sequence of values; and
  dividing (S130) each of the calculated distances by a difference between a value of a function of the corresponding value of the scan parameter ($\theta$, $\varphi$) and a value of the function of the adjacent value of the scan parameter ($\theta$, $\varphi$) in the sequence to generate, for each of the values of the scan parameter ($\theta$, $\varphi$), a respective value of the conversion factor ($CF_h$, $CF_v$) that is indicative of the simulated rate of change of distance across the portion of the eye (280) with the function of the scan parameter ($\theta$, $\varphi$).

E10. The computer-implemented method according to E9, wherein the computer simulation uses biological measurements of the eye (280) to model ray propagation through the model of the eye (280) and the model of the ocular imaging apparatus (200).

E11. The computer-implemented method according to any of E8 to E10, further comprising determining a distance between the designated ocular features in the imaged region by:
  receiving (S40) a designation of a first pixel (136-1) of the pixels in the digital image (132) which represents a first ocular feature in the region of the eye (280), and a designation of a second pixel (136-2) of the pixels in the digital image (132) which represents a second ocular feature in the region of the eye (280); and
  using the determined value of the conversion factor ($CF_h$, $CF_v$) to convert a distance (138) between the first pixel (136-1) and the second pixel (136-2) in the digital image (132) to a distance between the first ocular feature and the second ocular feature in the region of the eye (280).

E12. The computer-implemented method according to any of E8 to E11, wherein the portion of the eye comprises a retina of the eye (280), and the mapping relates values of the scan parameter ($\theta$, $\varphi$), which span a range of scan parameter ($\theta$, $\varphi$) values covered in a wide-field scan of the retina by the ocular imaging apparatus (200), to respective values of the conversion factor (CF$_h$, CF$_v$).

E13. The computer-implemented method according to any of E8 to E12, wherein
ophthalmic optical coherence tomography, OCT, imaging data generated by a controller (205) of an OCT imaging apparatus is processed as the ocular imaging data, and
the obtaining (S10) comprises obtaining from the OCT imaging data a value of a scan parameter (θ, φ) of the OCT imaging apparatus which is indicative of an OCT scan location in the eye (280) of an OCT scan performed by the OCT imaging apparatus to acquire a digital OCT image of the imaged region of the portion of the eye (280).

E14. A computer-implemented method of generating a mapping which relates values of a scan parameter (θ, φ) of an ocular imaging apparatus (200) that are indicative of respective scan locations in a portion of an eye (280) at which an ocular imaging apparatus (200) is operable to acquire digital images of respective imaged regions of the portion of the eye (280), to respective values of a conversion factor (CF$_h$, CF$_v$) for calculating a distance between designated ocular features in the respective imaged regions of the portion of the eye (280), the method comprising:
running (S110) a computer simulation of light ray propagation through a model of the ocular imaging apparatus (200) and a model of the eye (280) to generate simulation results which relate each value of the scan parameter (θ, φ) in a sequence of the values of the scan parameter (θ, φ) to a corresponding location in a portion of the model of the eye (280) onto which a ray of light propagating through the model of the ocular imaging apparatus (200) impinges when the model of the ocular imaging apparatus (200) operates in accordance with the value of the scan parameter (θ, φ);
calculating (S120), for each of the values of the scan parameter (θ, φ), a distance between the corresponding location in the portion of the model of the eye (280) and a location in the portion of the model of the eye (280) corresponding to an adjacent value in the sequence of values; and
dividing each of the calculated distances by a difference between a value of a function of the corresponding value of the scan parameter and a value of the function of the adjacent value of the scan parameter (θ, φ) in the sequence to generate, for each of the values of the scan parameter (θ, φ), a respective value of the conversion factor (CF$_h$, CF$_v$) that is indicative of a rate of change of distance across the portion of the eye (280) with the function of the scan parameter (θ, φ).

E15. A computer program (390) comprising computer-readable instructions which, when executed by a computer processor (320), cause the computer processor (320) to execute the method according to at least one of E8 to E14.

The example aspects described herein avoid limitations, specifically rooted in computer technology, relating to conventional techniques for calculating ocular feature size in ocular image processing. For example, the use of known coordinate remapping approaches to calculating ocular feature size can involve slow, resource-intensive calculations that are particularly problematic in applications where narrow-field images of the retina or other portion of the eye are acquired at a high frame rate, for example, so that many of the relatively complex remapping and subsequent distance calculations need to be performed. The techniques described herein, on the other hand, enable the distances between designated ocular features in retinal images to be accomplished substantially faster and in a more computationally efficient manner, using less computer processing and memory resources, relative to the conventional techniques, by use of the determined conversion factor value. Also, by virtue of the foregoing capabilities of the example aspects described herein, which are rooted in computer technology, the example aspects described herein improve computers and computer processing/functionality, and also improve the field(s) of at least image processing, OCT, and data processing.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized in ways other than those shown in the accompanying figures.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Having now described some illustrative embodiments and embodiments, it is apparent that the foregoing is illustrative and not limiting, having been presented by way of example.

The apparatuses described herein may be embodied in other specific forms without departing from the characteristics thereof. The foregoing embodiments are illustrative rather than limiting of the described systems and methods. Scope of the apparatuses described herein is thus indicated by the appended claims, rather than the foregoing description, and changes that come within the meaning and range of equivalence of the claims are embraced therein.

The invention claimed is:

1. A mapping generator module configured to generate a mapping which relates values of a scan parameter ($\theta$, $\varphi$) of an ocular imaging apparatus that are indicative of respective scan locations in a portion of an eye at which an ocular imaging apparatus is operable to acquire digital images of respective imaged regions of the portion of the eye, to respective values of a conversion factor ($CF_h$, $CF_v$) for calculating a distance between designated ocular features in the respective imaged regions of the portion of the eye, the mapping generator module being configured to generate the mapping by:
   running a computer simulation of light ray propagation through a model of the ocular imaging apparatus and a model of the eye to generate simulation results which relate each value of the scan parameter ($\theta$, $\varphi$) in a sequence of the values of the scan parameter ($\theta$, $\varphi$) to a corresponding location in a portion of the model of the eye onto which a ray of light propagating through the model of the ocular imaging apparatus impinges when the model of the ocular imaging apparatus operates in accordance with the value of the scan parameter ($\theta$, $\varphi$);
   calculating, for each of the values of the scan parameter ($\theta$, $\varphi$), a distance between the corresponding location in the portion of the model of the eye and a location in the portion of the model of the eye corresponding to an adjacent value in the sequence of values; and
   dividing each of the calculated distances by a difference between a value of a function of the corresponding value of the scan parameter and a value of the function of the adjacent value of the scan parameter ($\theta$, $\varphi$) in the sequence to generate, for each of the values of the scan parameter ($\theta$, $\varphi$), a respective value of the conversion factor ($CF_h$, $CF_v$) that is indicative of a rate of change of distance across the portion of the eye with the function of the scan parameter ($\theta$, $\varphi$).

2. An apparatus for processing ocular imaging data generated by a controller of an ocular imaging apparatus to evaluate a conversion factor for calculating a distance between designated ocular features in an at least one imaged region of a portion of an eye the apparatus comprising:
   a scan parameter obtaining module configured to obtain from the ocular imaging data values of a scan parameter ($\theta$, $\varphi$) of the ocular imaging apparatus which are indicative of respective scan locations in a portion of the eye of a scan performed by the ocular imaging apparatus to acquire digital images of respective imaged regions of the portion of the eye;
   a mapping generator module configured to generate a mapping which relates the values of the scan parameter ($\theta$, $\varphi$) to respective values of a conversion factor ($CF_h$, $CF_v$) for calculating a distance between designated ocular features in the respective imaged regions of the portion of the eye, the mapping generator module being configured to generate the mapping by:
      running a computer simulation of light ray propagation through a model of the ocular imaging apparatus and a model of the eye to generate simulation results which relate each value of the scan parameter ($\theta$, $\varphi$) in a sequence of the values of the scan parameter ($\theta$, $\varphi$) to a corresponding location in a portion of the model of the eye onto which a ray of light propagating through the model of the ocular imaging apparatus impinges when the model of the ocular imaging apparatus operates in accordance with the value of the scan parameter ($\theta$, $\varphi$),
      calculating, for each of the values of the scan parameter ($\theta$, $\varphi$), a distance between the corresponding location in the portion of the model of the eye and a location in the portion of the model of the eye corresponding to an adjacent value in the sequence of values, and
      dividing each of the calculated distances by a difference between a value of a function of the corresponding value of the scan parameter and a value of the function of the adjacent value of the scan parameter ($\theta$, $\varphi$) in the sequence to generate, for each of the values of the scan parameter ($\theta$, $\varphi$), a respective value of the conversion factor ($CF_h$, $CF_v$) that is indicative of a rate of change of distance across the portion of the eye with the function of the scan parameter ($\theta$, $\varphi$);
   a conversion factor evaluation module configured to use the obtained values of the scan parameter ($\theta$, $\varphi$), and the mapping generated by the mapping generator module to determine a respective value of the conversion factor ($CF_h$, $CF_v$) for converting a distance between pixels in the digital image, whose respective pixels values are acquired during imaging of the region by the ocular imaging apparatus using different respective values of the scan parameter ($\theta$, $\varphi$), to a distance between corresponding locations in the region of the eye; and
   a data storage module configured to store the digital image in association with the determined value of the conversion factor ($CF_h$, $CF_v$).

3. The apparatus according to claim 2, wherein the mapping generator module is configured to use biological measurements of the eye to model light ray propagation through the model of the eye and the model of the ocular imaging apparatus in the computer simulation.

4. The apparatus according to claim 2 or claim 3, further comprising a distance calculator module configured to determine a distance between the designated ocular features in the imaged region of the eye by:
   receiving a designation of a first pixel of the pixels in the digital image which represents a first ocular feature in the region of the eye and a designation of a second pixel of the pixels in the digital image which represents a second ocular feature in the region of the eye; and
   using the determined value of the conversion factor ($CF_h$, $CF_v$) to convert a distance between the first pixel and the second pixel in the digital image to a distance between the first ocular feature and the second ocular feature in the region of the eye.

5. The apparatus according to claim 2, wherein the portion of the eye comprises a retina of the eye.

6. The apparatus according to claim 5, wherein the mapping relates values of the scan parameter, which span a range of scan parameter values covered in a wide-field scan of the retina by the ocular imaging apparatus, to respective values of the conversion factor ($CF_h$, $CF_v$).

7. The apparatus according to claim 2, wherein
   the apparatus is configured to process, as the ocular imaging data, ophthalmic optical coherence tomography, OCT, imaging data generated by a controller of an OCT imaging apparatus, and
   the scan parameter obtaining module is configured to obtain from the OCT imaging data a value of a scan parameter ($\theta$, $\varphi$) of the OCT imaging apparatus which is indicative of an OCT scan location in the eye of an OCT scan performed by the OCT imaging apparatus to acquire a digital OCT image of the imaged region of the portion of the eye.

8. A computer-implemented method of generating a mapping which relates values of a scan parameter ($\theta$, $\varphi$) of an ocular imaging apparatus that are indicative of respective scan locations in a portion of an eye at which an ocular imaging apparatus is operable to acquire digital images of respective imaged regions of the portion of the eye, to respective values of a conversion factor ($CF_h$, $CF_v$) for calculating a distance between designated ocular features in the respective imaged regions of the portion of the eye, the method comprising:

running a computer simulation of light ray propagation through a model of the ocular imaging apparatus and a model of the eye to generate simulation results which relate each value of the scan parameter ($\theta$, $\varphi$) in a sequence of the values of the scan parameter ($\theta$, $\varphi$) to a corresponding location in a portion of the model of the eye onto which a ray of light propagating through the model of the ocular imaging apparatus impinges when the model of the ocular imaging apparatus operates in accordance with the value of the scan parameter ($\theta$, $\varphi$);

calculating, for each of the values of the scan parameter ($\theta$, $\varphi$), a distance between the corresponding location in the portion of the model of the eye and a location in the portion of the model of the eye corresponding to an adjacent value in the sequence of values; and dividing each of the calculated distances by a difference between a value of a function of the corresponding value of the scan parameter and a value of the function of the adjacent value of the scan parameter ($\theta$, $\varphi$) in the sequence to generate, for each of the values of the scan parameter ($\theta$, $\varphi$), a respective value of the conversion factor ($CF_h$, $CF_v$) that is indicative of a rate of change of distance across the portion of the eye with the function of the scan parameter ($\theta$, $\varphi$).

9. The computer-implemented method according to claim 8, further comprising processing ocular imaging data generated by a controller of the ocular imaging apparatus to evaluate a conversion factor ($CF_h$, $CF_v$) for calculating a distance between designated ocular features in an imaged region of a portion of an eye, by:

obtaining from the ocular imaging data a value of a scan parameter ($\theta$, $\varphi$) of the ocular imaging apparatus which is indicative of a scan location in the eye of a scan performed by the ocular imaging apparatus to acquire a digital image of the imaged region of the portion of the eye;

using the obtained value of the scan parameter ($\theta$, $\varphi$), and the mapping to determine a respective value of the conversion factor ($CF_h$, $CF_v$) for converting a distance between pixels in the digital image, whose respective pixels values are acquired during imaging of the region by the ocular imaging apparatus using different respective values of the scan parameter ($\theta$, $\varphi$), to a distance between corresponding locations in the region of the eye; and storing the digital image in association with the determined value of the conversion factor ($CF_h$, $CF_v$).

10. The computer-implemented method according to claim 9, further comprising determining a distance between the designated ocular features in the imaged region by:

receiving a designation of a first pixel of the pixels in the digital image which represents a first ocular feature in the region of the eye, and a designation of a second pixel of the pixels in the digital image which represents a second ocular feature in the region of the eye; and using the determined value of the conversion factor ($CF_h$, $CF_v$) to convert a distance between the first pixel and the second pixel in the digital image to a distance between the first ocular feature and the second ocular feature in the region of the eye.

11. The computer-implemented method according to claim 9 wherein ophthalmic optical coherence tomography, OCT, imaging data generated by a controller of an OCT imaging apparatus is processed as the ocular imaging data, and the obtaining comprises obtaining from the OCT imaging data a value of a scan parameter ($\theta$, $\varphi$) of the OCT imaging apparatus which is indicative of an OCT scan location in the eye of an OCT scan performed by the OCT imaging apparatus to acquire a digital OCT image of the imaged region of the portion of the eye.

12. The computer-implemented method according to claim 8, wherein the computer simulation uses biological measurements of the eye to model ray propagation through the model of the eye and the model of the ocular imaging apparatus.

13. The computer-implemented method according to claim 8, wherein the portion of the eye comprises a retina of the eye, and the mapping relates values of the scan parameter ($\theta$, $\varphi$), which span a range of scan parameter ($\theta$, $\varphi$) values covered in a wide-field scan of the retina by the ocular imaging apparatus, to respective values of the conversion factor ($CF_h$, $CF_v$).

14. A computer program comprising computer-readable instructions which, when executed by a computer processor cause the computer processor to execute the method according to claim 8.

* * * * *